(12) United States Patent
Kvitnitsky et al.

(10) Patent No.: US 7,838,037 B2
(45) Date of Patent: *Nov. 23, 2010

(54) METHOD OF MICROENCAPSULATION

(75) Inventors: Emma Kvitnitsky, Kiryat Shmona (IL); Yury Shapiro, Givat Shmuel (IL); Olga Privalov, Kiryat Yam (IL); Irena Oleinik, Maalot (IL); Igor Polisher, Kiryat Haim (IL)

(73) Assignee: Tagra Biotechnologies Ltd., Netanya (IL)

(*) Notice: Subject to any disclaimer, the term of this patent is extended or adjusted under 35 U.S.C. 154(b) by 132 days.

This patent is subject to a terminal disclaimer.

(21) Appl. No.: 11/208,007

(22) Filed: Aug. 22, 2005

(65) Prior Publication Data

US 2006/0051425 A1 Mar. 9, 2006

Related U.S. Application Data

(63) Continuation-in-part of application No. 10/130,529, filed as application No. PCT/IL00/00759 on Nov. 16, 2000, now Pat. No. 6,932,984.

(30) Foreign Application Priority Data

Nov. 17, 1999 (GB) ................................. 9927202.3

(51) Int. Cl.
| | |
|---|---|
| A61J 3/07 | (2006.01) |
| A61J 9/50 | (2006.01) |
| A61K 6/083 | (2006.01) |
| A61K 8/72 | (2006.01) |
| A61K 9/14 | (2006.01) |
| A61K 9/16 | (2006.01) |
| A61K 9/127 | (2006.01) |
| B01J 13/02 | (2006.01) |
| B01J 13/04 | (2006.01) |
| B01J 13/18 | (2006.01) |
| B05D 7/00 | (2006.01) |
| B29C 39/10 | (2006.01) |
| B32B 25/00 | (2006.01) |
| B32B 5/16 | (2006.01) |
| B32B 9/00 | (2006.01) |
| B32B 15/02 | (2006.01) |
| B32B 17/02 | (2006.01) |
| B32B 19/00 | (2006.01) |
| B32B 21/02 | (2006.01) |
| B32B 23/02 | (2006.01) |
| B32B 27/00 | (2006.01) |
| B32B 27/02 | (2006.01) |

(52) U.S. Cl. .................. 424/490; 424/489; 424/493; 424/494; 424/495; 424/496; 424/497; 424/501; 264/4.33; 264/4.6; 264/4.1; 264/4.32; 264/4; 427/212; 427/213.3; 427/213.36; 427/213.31; 428/402.2; 428/402.21; 428/402.22; 428/402.24; 428/404; 428/407; 523/105

(58) Field of Classification Search ................ 264/4.33, 264/4.6; 424/490, 493, 494, 495, 497, 501, 424/489, 496; 427/212, 213.3, 213.36, 213.31; 428/402.2, 402.21, 402.22, 402.24, 404, 428/407; 523/105
See application file for complete search history.

(56) References Cited

U.S. PATENT DOCUMENTS

| | | | |
|---|---|---|---|
| 2,928,770 A | 3/1960 | Bardani | |
| 3,429,827 A | 2/1969 | Ruus | |
| 3,737,337 A | 6/1973 | Schnoring et al. | |
| 3,891,570 A | 6/1975 | Fukushima et al. | |
| 3,951,851 A | 4/1976 | Kitajima et al. | |
| 4,384,975 A | 5/1983 | Fong | |
| 4,861,627 A | 8/1989 | Mathiowitz et al. | |
| 5,026,559 A * | 6/1991 | Eichel et al. | ................ 424/458 |
| 5,792,477 A | 8/1998 | Rickey et al. | |
| 5,795,570 A | 8/1998 | Weber et al. | |
| 5,916,598 A | 6/1999 | Pickey et al. | |
| 5,985,354 A | 11/1999 | Mathiowitz et al. | |
| 6,511,749 B1 | 1/2003 | Mathiowitz et al. | |
| 6,528,035 B1 | 3/2003 | Mathiowitz et al. | |
| 6,599,627 B2 * | 7/2003 | Yeo et al. | ............... 428/402.21 |
| 6,932,984 B1 * | 8/2005 | Babtsov et al. | .............. 424/490 |
| 2003/0222378 A1 | 12/2003 | Xing et al. | |

FOREIGN PATENT DOCUMENTS

| | | |
|---|---|---|
| FR | 2 766 368 | 1/1999 |
| GB | 1 017 676 A | 1/1966 |
| GB | 1394780 | 5/1975 |
| WO | 90/13361 A | 11/1990 |
| WO | 01/35933 A2 | 5/2001 |

OTHER PUBLICATIONS

Reza Arshady., "Microspheres, Microcapsules and Liposomes" The MML Series, vol. 1: Preparation and Chemical Applications, (1999) pp. 76-79.

Simon Benita., "Microencapsulation: methods and industrial applications", Drugs and the pharmaceutical sciences; vol. 73 (1996) pp. 2-3.

Mao et al., "Effect of WOW process parameters on morphology and burst release of FITC-dextran loaded PLGA microspheres", Science Direct, International Journal of Pharmaceutics, V. 334, p. 137-148 (2007).

(Continued)

*Primary Examiner*—Patrick D Niland
(74) *Attorney, Agent, or Firm*—Browdy and Neimark, PLLC

(57) ABSTRACT

The present invention provides methods for microencapsulation of active ingredients for topical application, whereby double-layer and triple-layer microcapsules are obtained. The microcapsules protect the active ingredients, maintain their original activity throughout processing, formulation and storage, and enable controlled release of the active ingredient only upon application onto the skin.

69 Claims, 2 Drawing Sheets

OTHER PUBLICATIONS

Meng et al., "W/O/W double emulsion technique using ethyl acetate as organic solvent: effects of its diffusion rate on the characteristics of microparticles", Journal of Controlled Release 91, p. 407-416 (2003).

Park et al., "Dextran/PLGA Double-Layered Microspheres for Sustained Release of Doxorubicin", Tissue Engineering and Regenerative Medicine, vol. 6, No. 4-11, p. 588-594 (2009).

Pekarek et al., "Double-walled polymer microspheres for controlled drug release", Nature, vol. 367, p. 258-260 (1994).

Rosca et al. "Microparticle formation and its mechanism in single and double emulsion solvent evaporation", Journal of Controlled Release 99, p. 271-280 (2004).

Yuan, Junjie, "Organic Pigment Particles Coated with Colloidal Nano-Silica Particles Via Layer-By-Layer Assembly", Chemistry of Materials, Jun. 17, 2005, vol. 17, No. 14, pp. 3587-3594, XP008071479.

* cited by examiner

METHOD OF MICROENCAPSULATION

CROSS-REFERENCE TO RELATED APPLICATIONS

The present application is a continuation-in-part application of U.S. application Ser. No. 10/130,529, filed on Sep. 30,2002, under 35 U.S.C. 371, based on International Application No. PCT/IL00/00759, filed Nov. 16, 2000, in which the United States is designated, now U.S. Pat. No. 6,932,984 and claiming priority from Great Britain Application No. GB 9927202.3, filed Nov. 17, 1999, the entire contents of each and all these applications being hereby incorporated by reference herein in their entirety as if fully disclosed herein.

FIELD OF THE INVENTION

The present invention relates to methods of microencapsulation of active ingredients such as agents having biological activity, odor agents and color agents for topical applications. The microcapsules obtained according to the provided methods are single-layer or multi-layer, preferably double-layer, microcapsules, that maintain the original activity of the encapsulated agents and enable controlled release of the active ingredient only when applied topically.

BACKGROUND OF THE INVENTION

The art of microencapsulation has been the object of considerable attention in recent years in view of the increased necessity to maintain a reactive substance in an inert stage until the time it is required to perform a given function. Microencapsulation provides a number of benefits, the most outstanding being the capability of microcapsules to protect sensitive substances against chemical and physical degradation, to allow separation of substances which are harmful upon contact with each other, to mask an original odor, color or taste of a substances, to control dispersibility of substances, and to prevent undesirable release of an encapsulated substance to the formulation that contains it.

Microcapsules are available usually in powder form and consist of spherical particles, which contain an encapsulated (entrapped) substance. The spherical particle usually consists of a polymeric shell and the encapsulated substance is located within the shell. The polymeric shell is frequently applied as a wall-forming material and serves as a membrane for the encapsulated substance. This membrane may be semi-permeable or degradable, and therefore it allows the microcapsule to be an efficient tool for controlled release applications.

Microencapsulation itself has various advantages. Microcapsules protect sensitive substances from degradation processes and provide means for controlled release of desired active substances. It also enables the conversion of liquids to powders and is used to isolate substances that are otherwise detrimental when in contact with each other.

Numerous techniques for microencapsulation are available depending on the nature of the encapsulated substance and on the type of polymer used. A widely used method for encapsulation of water insoluble substances such as some vitamins, drugs and oils within water insoluble polymers is the solvent removal method. Generally in such a process the desired polymer is dissolved in a suitable organic solvent. This action is followed by addition of the desired substance to be encapsulated. This substance is either dissolved or dispersed in the organic solvent. The resulting organic solution or dispersion is dispersed in an aqueous phase to obtain an oil-in-water emulsion where oily microparticles are dispersed in the aqueous phase. Upon complete removal of the solvent from the microparticles, the microcapsules are formed.

Several patents describe methods of removing the solvent. U.S. Pat. No. 4,384,975 describes the removal of the solvent by vacuum distillation. In GB 1,394,780 the removal of the solvent is done by evaporation. In U.S. Pat. No. 3,891,570, the removal of the polymer solvent is carried out by heating the aqueous dispersion or by reducing its pressure, In U.S. Pat. No. 3,737,337 the removal of the organic solvent is done by extraction with water, however it is limited to certain solvent systems.

Microencapsulation is suitable for a large variety of materials including drugs, vitamins and food supplements, since this process is easily adaptable by varying the solvents and/or the polymers. Some microencapsulation technologies may yield microcapsules having desirable size, spherical shape and smooth surface—properties important for controlled release, for chemical stability of the core material, and homogeneous delivery of stable active substances to the target area.

A basic prerequisite for this process is the use of a solvent that is able to efficiently dissolve the biologically active substance to be encapsulated as well as the wall-forming material. This solvent has to be only partially soluble in water, giving rise to emulgation of an organic phase in a continuous water phase. Chlorinated solvents such as dichloromethane and chloroform as well as glycols or their mixtures with other solvents have been widely used since they facilitate the microencapsulation process.

However, all the microencapsulation technologies based on solvent systems such as chlorinated solvents are not applicable and are quite inappropriate for food, cosmetics, pharmaceutical, dental and oral products, since they do not meet FDA and other regulations due to the presence of residual amounts of chlorinated solvents in the microcapsules. Simple vacuum or heat drying do not result in a sufficiently low chlorinated solvent content so as to meet FDA regulations, thus creating an essential necessity for a method for encapsulating vitamins, food supplements, oils or pharmaceuticals by the solvent removal technique.

U.S. Pat. No. 6,599,62 discloses a solvent exchange method in order to obtain single-wall microcapsules of pharmaceuticals. The described method is based on an exchange of water and a non-chlorinated organic solvent such as acetic acid, ethyl acetate, methyl acetate, or ethyl formate to form a biodegradable poly(lactic acid-co-glycolic acid) (PLGA) shell around an aqueous drug core. All these solvents meet the FDA regulations.

Few patents disclose techniques for obtaining multi-wall microspheres and microcapsules by various coating processes, which do not apply the solvent removal method, or apply spray-drying technique in the case of volatile organic solvents. U.S. Pat. No. 3,429,827 describes coating of the inner microcapsules with a second polymer shell by spray-drying or interfacial condensation methods. U.S. Pat. No. 4,861,627 describes a single-step method for preparation of multi-wall microspheres from a mixture of any two or three polymers selected from polyanhydrides, polyorthoesters, poly(lactic acid), polystyrene, polyamides, polybutadiene, polyurethanes, and copolymers, which are not soluble in each other but are soluble in a volatile organic solvent. The mixture is suspended in an aqueous solution followed by slow spray-drying of volatile solvent, creating microspheres with an inner core formed by one polymer and an outer layer formed by a second polymer. U.S. Pat. Nos. 5,985,354, 6,511,749 and 6,528,035 disclose preparation of multi-wall polymer microspheres by a similar technique, from hydrophilic, water-soluble polymers that are not soluble in each other at a particular concentration and temperature but have a positive spreading coefficient in solution. U.S. Pat. No. 5,795,570 describes the formation of a second semi-permeable membrane, which is made of polysaccharide gum such as an alkali metal alginate, comprising core microcapsules. More specifically, U.S. patent Publication No. 2003/0222378 discloses microencapsulation of a series of paraffin compounds with an interfacial polymerization process to form double-shell microcapsules with relatively low shell permeability. The inner shell was formed by a reaction between poly(propylene glycol) and bifunctional polyisocyanates, and the outer shell by a reaction between bifunctional polyisocyanates and polyamines that were added to the continuous aqueous phase.

In summary, none of the methods known in the art meets the growing market requirements for a considerable protection factor of the encapsulated substance against oxidation and/or degradation and for the ability to control the release of the encapsulated substance. Hence, there is still a need for an advanced method for stable encapsulation of active substances that simultaneously affords control of its release from the microcapsules.

SUMMARY OF THE INVENTION

It is an object of the present invention to provide methods for production of microcapsules for topical application, wherein the microcapsules consist of a core of an encapsulated substance and one or more outer polymeric shells.

It is another object of the present invention to provide microcapsules for topical application in which the encapsulated active ingredient in the inner core is stable throughout the preparation of the microcapsules, their incorporation into formulations and storage.

It is another object of the present invention to provide microcapsules for topical application that are similar in size and shape and are homogeneously dispersed in all types of formulations.

It is a further object of the present invention to provide microcapsules for topical application with an optimal controlled release system that delivers a high content of the active ingredient only upon application onto the skin/scalp.

In one embodiment, the present invention provides a method for the production of single-layer microcapsules for topical application, wherein the microcapsules consist of a core made of an encapsulated active ingredient and an outer polymer-plasticizer shell, wherein said polymer is a wall-forming polymer.

In another embodiment, the present invention provides a method for the production of microcapsules for topical application, wherein the microcapsules consist of an inner core microcapsule which contains an active ingredient located within a wall-forming polymer and one or more outer shells of the same or different wall-forming polymer coating the inner core microcapsule.

In a preferred embodiment, the present invention provides a method for the production of double-layer microcapsules.

One of the advantages of the method of the present invention consists in its universal application, namely, the technology may be applied for encapsulation and stabilization of degradable oil-soluble and oil-dispersible compounds useful in the cosmetic and pharmaceutical industries.

The active ingredient for encapsulation according to the invention may be organic or inorganic, natural or synthetic, substances such a, but not limited to, vitamins, natural extracts, essential oils, individual compounds prepared synthetically or isolated from a natural source, pigments, fragrances, color agents and volatile natural and synthetic compounds.

The method of the present invention increases the stability of highly sensitive substances against degradation, can mask an original color or undesirable odor of a substance, and prevents undesirable release of the encapsulated substance into the formulation that contains it.

Also provided by the present invention are single-layer, double-layer and multi-layer microcapsules obtained by the methods of the invention and compositions for topical application for skin care, skin supplement, hair care, sun care, baby care, oral hygiene and oral care, and pharmaceutical compositions for topical application comprising said microcapsules.

BRIEF DESCRIPTION OF THE FIGURES

(FIG. 1A) and at 40° C. (FIG. 1B).

DETAILED DESCRIPTION OF THE INVENTION

Figure 1A:
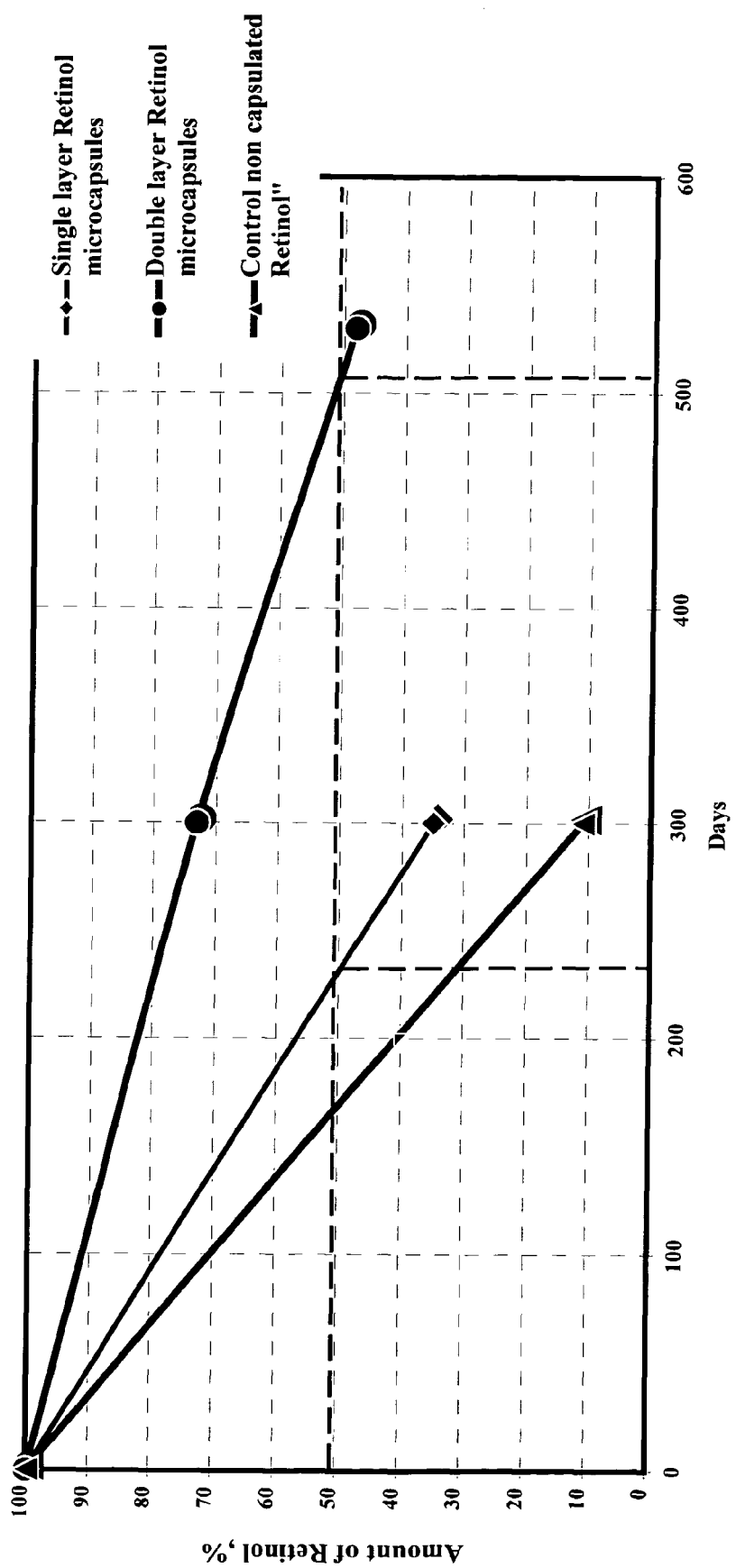
FIGS. 1A-1B illustrate the effectiveness of protection of Retinol from oxidation when encapsulated in single-layer or double-layer microcapsules of the invention in comparison to non-encapsulated Retinol. Measurements of oxidation kinetics were tested at 25° C.

The term "microcapsule", as used herein, refers to a spherical microparticle consisting of a polymeric shell serving as a wall-forming material and an encapsulated active substance located within the shell. This term is distinct from microspheres, which consist of spherical homogeneous granules of the active substance dispersed in a polymer and are, in strict sense, spherically empty particles.

The term "single-layer microcapsule" refers to a microcapsule consisting of a single polymeric shell and the encapsulated active substance located within the shell in the center of the microcapsule.

The term "inner core microcapsule" refers to a single-layer microcapsule as defined above when within a double-layer or multi-layer microcapsule.

The term "multi-layer microcapsule" refers to a microcapsule consisting of an inner core microcapsule and one or more outer polymeric shells. The term "double-layer microcapsule" refers to a microcapsule consisting of the inner core microcapsule coated with a second polymeric shell. In the course of the microencapsulation, the core microcapsules are introduced to the polymer-plasticizer solution or polymer-mineral dispersion, and promote the formation of "embryo" shells, which are converted to a structured solid shell of double-layer microcapsules.

The term "wall-forming polymer" typically refers to a polymer or a combination of two or more different polymers as defined herein, which form a component of the external wall or layer or shell of the microcapsules.

The term "polymer shell" refers to a polymer layer containing the wall-forming polymer and, optionally, further components such as a plasticizer and/or a mineral. The term "polymer-plasticizer shell" refers to a polymer shell containing a plasticizer. The term "polymer-mineral shell" refers to a polymer shell containing a mineral.

The term "composite double-layer or multi-layer microcapsule" refers to a microcapsule in which the inner or outer shell is a polymer-mineral shell.

The term "powdered modified core microcapsule" refers to the inner core microcapsule or the double-layer or multi-layer microcapsule treated with a material able to modify the morphology of the surface of microcapsule and to increase the specific surface area (SSA) of the outer microcapsule's shell up to a level that enables building of a next polymer-plasticizer or polymer-mineral shell on said modified outer shell due to increased adhesion between the two shells.

The term "partially miscible in water" should be understood as relating to the property of being able to be dissolved in water in concentrations while lower than a certain critical concentration, while the concentration thereof increases above a certain critical value, there is phase separation and the water and the organic solvents form two separate phases. An example of such an organic solvent is ethyl acetate or ethyl formate.

The term "saturated" should be understood as referring to a solution that contains the organic solvent in a concentration about the critical value or slightly below, namely, a saturated solution contains a concentration of the organic solvent close to the maximal concentration before phase separation occurs. However, the term "saturated" should not be understood in a limiting fashion in that at times, also a solution containing less than 90%, and at times even about 80% of the critical concentration may be considered as saturated for the purpose of the invention. The emulsifier used in stage (b) may either be a priori dissolved in the aqueous solution or may be added to the aqueous solution simultaneously or after mixing of the organic solution therewith.

The term "agitation" should be understood as referring to steering, shaking, vibrating and in general to any process whereby mechanical energy is transferred to the liquid to cause some turbulence in the liquid.

The terms "active ingredient" or "active substance" are used herein interchangeably and refer to the material located within the inner core microcapsule, which material may include one or more agents having biological activity, an odor agent or a color agent, and may include non-active ingredients such as an anti-oxidant, a plasticizer, a carrier, etc.

The term "topical application" as used herein refers to external application to the skin, mucous membranes, teeth, hair, or scalp. The term "compositions for topical application" includes compositions in any form such as ointment, paste, cream or lotion intended for skin care, skin supplement, sun care, baby care, hair care, oral hygiene (e.g., toothpaste, mouthwash), pharmaceutical compositions for topical application, and similar compositions.

The microencapsulation methods of the present invention are based on the solvent removal method.

In one aspect, the present invention relates toga method for the production of microcapsules for topical application, wherein the microcapsules consist of a core made of an encapsulated active ingredient and one or more shells of the same or different wall-forming polymer, said method comprising the steps of:

(a) dissolving or dispersing the active ingredient, optionally together with an antioxidant, a plasticizer or both, in an organic solvent of a kind that is partially miscible with water and is capable of dissolving or dispersing said substance, together with a wall-forming polymer selected from the group consisting of a polyacrylate, a polymethacrylate, low molecular weight poly(methyl methacrylate)-co-(methacrylic acid) (1:0.16), poly(ethyl acrylate)-co-(methyl methacrylate)-co-(trimethylammonium-ethyl methacrylate chloride) (1:2:0.1), poly(butyl methacrylate)-co-(2-dimethylaminoethyl methacrylate)-co-(methyl methacrylate) (1:2:1), poly(styrene)-co-(maleic anhydride), copolymer of octylacrylamide, cellulose ethers, cellulose esters and poly(ethylene glycol)-block-poly (propylene glycol)-block-poly(ethylene glycol), to form an organic solution or dispersion;

(b) preparing an aqueous continuous phase saturated with said organic solvent and comprising an emulsifier;

(c) while agitating, pouring the organic solution or dispersion obtained in (a) into the aqueous continuous phase obtained in (b), to form an emulsion;

(d) adding an excess amount of water to the emulsion obtained in (c) to initiate extraction of the organic solvent from the emulsion, and optionally incubating for further extraction of the solvent and formation of solid microcapsules (hereinafter "the core microcapsules");

(e) either (i) isolating the core microcapsules, washing with water and drying, or (ii) immersing the core microcapsules into an aqueous solution of alcohol, separating the core microcapsules and drying, thus obtaining single-layer microcapsules; and (f) if desired, treating the surface of the core single-layer microcapsules obtained in (e) with a material that modifies the morphology of the core surface, increases the specific surface area and facilitates the adhesion of an additional polymeric shell, and repeating steps (a) to (e) to form double-layer microcapsules, or repeating steps (a) to (f) to add two or more additional layers around the core microcapsule, thereby obtaining multi-layer microcapsules.

When the method is stopped in step (e), single-layer microcapsules are obtained. If a plasticizer is added in step (a), the obtained single-layer microcapsules have an outer polymer-plasticizer shell.

These single-layer microcapsules can effectively protect active ingredients such as vitamins, oils, natural extracts, essential oils, color agents such as pigments and colorants, odor agents such as fragrances, and pharmaceuticals for topical application such as antibiotics.

In one embodiment, the active ingredient of the single-layer microcapsules is a plant or herbal oil such as Evening Primrose Oil, Borage Oil, Sea Buckthorn Oil (*Hippophae rhamnoides*) Oil and Tea Tree Oil.

In another embodiment, the active ingredient of the single-layer microcapsules is an antibiotic such as, but not limited to, a macrolide antibiotic. selected from Erythromycin, Clarithromycin and Azithromycin.

The invention also provides single-layer microcapsules for oral hygiene having an outer polymer-plasticizer shell obtained by the method of the invention, wherein the wall-forming polymer is ethylcellulose and the active ingredient is a vitamin such as Retinol Palmitate or Tocopherol or a plant oil such as Hippophae Oil or Tea Tree Oil.

The microcapsules of the invention are effective in the protection of unstable and/or volatile substances and in the masking of colors and malodor. The effectiveness of protection/masking by single-layer microencapsulation depends on the chemical structure, molecular weight and physical properties of the microencapsulated active ingredient. For some active substances used in topical compositions, the known methods of single-layered microencapsulation do not provide an adequate protection from degradation and/or masking effects. For such actives, a double- or multi-layered microencapsulation may be required in order to obtain an effective protection and/or masking of original odor/color of the target substance for encapsulation.

Thus, in another aspect, the present invention relates to a method for the production of multi-layer microcapsules for topical application consisting of an inner core microcapsule comprising an active substance within a wall-forming polymer shell, and one or more outer shells of the same, or different wall-forming polymers coating the inner core microcapsule.

In general, the method for the preparation of multi-layer microcapsules according to the present invention consists of four main stages:

(i) preparation of the inner core microcapsules by the solvent removal method as described above for the single-layer microcapsules, using one or more appropriate wall-forming polymers;

(ii) treatment of the surface of said core microcapsules with a material that modifies the morphology of the core microcapsule surface and increases its specific surface area, thus obtaining powdered modified inner core microcapsules that facilitate the adhesion of a next polymeric layer;

(iii) preparation of double-layer microcapsules by coating the powdered modified inner core microcapsules obtained in stage (ii) with either a polymer-plasticizer shell, thus obtaining double-layer microcapsules, or a polymer-mineral shell, thus obtaining composite double-layer microcapsules; and (iv) repeating stages (ii) and (iii) to form additional layers around the core microcapsules according to the desired number of layers.

Thus, in one embodiment, the present invention relates to a method for the production of multi-layer microcapsules for topical application, wherein the microcapsules consist of an inner core microcapsule which contains an active ingredient located within a wall-forming polymer shell and one or more outer shells of the same or different wall-forming polymer coating the inner core microcapsule, said method comprising the steps of:

(a) dissolving or dispersing the active ingredient, optionally together with an antioxidant, a plasticizer or both, in an organic solvent of a kind that is partially miscible with water and is capable of dissolving or dispersing said substance, together with a wall-forming polymer selected from the group consisting of a polyacrylate, a polymethacrylate, low molecular weight poly(methyl methacrylate)-co-(methacrylic acid) (1:0.16), poly(ethyl acrylate)-co-(methyl methacrylate)-co (trimethylammonium-ethyl methacrylate chloride) (1:2:0.1), poly(butyl methacrylate)-co-(2-dimethylaminoethyl methacrylate)-co-(methyl methacrylate) (1:2:1), poly(styrene)-co-(maleic anhydride), copolymer of octylacrylamide, cellulose ethers, cellulose esters and poly(ethylene glycol)-block-poly(propylene glycol)-block-poly(ethylene glycol), to form an organic solution or dispersion;

(b) preparing an aqueous continuous phase saturated with said organic solvent and comprising an emulsifier;

(c) while agitating, pouring the organic solution or dispersion obtained in (a) into the aqueous continuous phase obtained in (b), to form an emulsion;

(d) adding an excess amount of water to the emulsion obtained in (c) to initiate extraction of the organic solvent from the emulsion, and optionally incubating for further extraction of the solvent and formation of solid microcapsules (hereinafter "the inner core microcapsules");

(e) either (i) isolating the inner core microcapsules, washing with water and drying, or (ii) immersing the core microcapsules into an aqueous solution of alcohol, separating the core microcapsules and drying;

(f) treating the surface of the dried inner core microcapsules obtained in (e) with a material that modifies the morphology of the surface, increases its specific surface area and facilitates the adhesion of an additional polymer shell, thus obtaining microcapsules powdered with said material (hereinafter "powdered modified inner cores");

(g) dissolving or dispersing a wall-forming polymer with a plasticizer or a mineral in an organic solvent of a kind that is partially miscible with water, to form a polymer-plasticizer solution or polymer-mineral dispersion;

(h) preparing an aqueous continuous phase saturated with said organic solvent and comprising an emulsifier;

(i) while agitating, pouring the polymer-plasticizer solution or polymer-mineral dispersion obtained in step (g) into the aqueous continuous phase obtained in step (h), to form a polymer-plasticizer emulsion or a polymer-mineral suspoemulsion;

(j) while agitating, immersing the powdered modified inner cores obtained in step (f) into the polymer-plasticizer emulsion or polymer-mineral suspo-emulsion obtained in step (i), forming a multi-component emulsion or a new suspo-emulsion, in which a formation of "embryo" shells around said core microcapsules is initiated;

(k) while stirring, either (i) adding an excess amount of water to the multi-component emulsion or the new suspoemulsion obtained in step (j), or (ii) pouring the multi-component emulsion or the new suspo-emulsion obtained in step (j) into water, and incubating the system for extraction of the organic solvent from said multi-component emulsion or suspo-emulsion, and conversion of the "embryo" shell into a solid polymer wall and formation of double-layer microcapsules;

(l) separating the obtained double-layer microcapsules from water and drying the wet capsules, thereby isolating double-layer microcapsules as a free flowing powder; and (m) if desired, repeating steps (f) to (l) to form one or more additional layers around the double-layer microcapsules, thereby obtaining multi-layer microcapsules.

In step (a) of the method of the invention, an organic solvent that is capable of dissolving or dispersing the active ingredient and the wall-forming materials is chosen. The solvent should be inactive with the dissolved material and can be selected from a variety of solvents such as ethyl acetate, ethanol, ethyl formate or other appropriate solvents approved by the FDA, or their mixtures. In a preferred embodiment, the solvent is ethyl acetate or its mixture with ethanol.

The active substance to be encapsulated by the present method, either a solid or a liquid, is then dissolved or dispersed in the organic solvent to form an organic solution or dispersion. If necessary (i.e., the active substance is sensitive to oxidation), an antioxidant such as butylated hydroxyanisole (BHA), butylated hydroxytoluene (BHT), or a mixture thereof, can be added at this stage for encapsulation with the active substance.

In order to control the physical properties and level of elasticity of the final microcapsules, it is a preferred embodiment to add at this stage also a plasticizer, such as tricaprylin, trilaurin, tripalmitin, triacetin, triethyl citrate, acetyltriethyl citrate, isopropyl myristate, paraffin oil, or a mixture thereof.

The wall-forming material, which may consist of one or more of said polymers defined in step (a), is then dissolved and/or dispersed in the organic solution/dispersion. In preferred embodiments, the wall forming polymer is ethyl cellulose, poly(methyl methacrylate)-co-(methacrylic acid) (1:0.16), poly(ethyl acrylate)-co-(methyl methacrylate)-co-(trimethylammonium-ethyl methacrylate chloride) (1:2:0.1), or a mixture thereof.

In step (b), an aqueous continuous phase is saturated by the same or different organic solvent (or mixture of solvents) used at the first stage. An appropriate emulsifier is added to the aqueous phase. Such an emulsifier may be selected from polyvinyl alcohol (PVA), sodium lauryl sulfate, lauryl phosphate, ethoxylated sorbates such as Tween-80, polyglycerol and poly(ethylene glycol), and their esters and ethers, or a mixture thereof. Said added emulsifier should be chosen and adapted to the system in such a way that it does not separate from water after the organic solvent is added in the next stage. It is advisable to adjust specifically the pH of the aqueous phase according to active substance and solvent properties.

In step (c), the organic solution/dispersion obtained in the first step, which contains the active substance and the wall-forming material, is poured into the aqueous continuous phase saturated with the organic solvent used in the first step, forming an emulsion. The pouring is done with agitation and the agitation is continued for a further period of time. The rate of mixing, type of mixer, and its duration affect, among other factors, the size of the formed droplets. The size of the formed droplets constitutes the basis for the final size of the microcapsules. It may be from 1 to 300 microns and may be controlled and tailored according to the intended use of the microcapsules, for example, preferably about 20-40 micron for topical application and 10-20 micron for dental application. Other factors responsible for the size of the formed droplets are the ratio of water to organic phase, temperature, quantity and kind of emulsifier.

In step (d), water is added to the emulsion formed in the previous step, for extracting the organic solvent. Preferably, the quantity of the water added is 10-30 times higher than the whole quantity of the organic solvent in the mixture. The most preferable ratio for optimal removal of the organic solvent is 20:1 (V/V water: solvent). Following the addition of the water, the mixture is incubated and agitated for several minutes up to a point where the main amount of the organic solvent is extracted into the water and equilibrium is reached. Typically, it takes 3 to 10 up to 15 minutes to reach equilibrium. Upon the gradual removal of the organic solvent, a solid polymer shell is formed surrounding the droplets of emulsion, thus enveloping all the ingredients (active substance, antioxidant, plasticizer), which are insoluble in the obtained solvent system (water with trace of organic solvent), inside of the formed solid core microcapsules. The formed microcapsules are then separated by sedimentation, filtration or centrifugation, subsequently washed with water and dried (step e).

The residue of ethyl acetate and similar solvents in raw materials for topical/dental products should meet the relevant regulations (FDA, Colipa, CTFA, etc.). It is necessary to remove the trace amounts of the organic solvent from the obtained microcapsules up to the limited level. In order to remove trace amounts of the solvent, the present invention presents an effective extraction technique. As defined in alternative step (e), the microcapsules obtained after filtration can be immersed in a 5% solution of ethanol in water for 2-12 hours, thereby causing the trace of organic solvent to be extracted from the microcapsules.

In step (f), the dried inner core microcapsules are treated with a material, e.g. silicon dioxide, boron nitride, magnesium silicate, that modifies the surface of the core microcapsules, changes its morphology, increases the specific surface area (SSA) (at least by 1.5 times), thus obtaining powdered modified inner core microcapsules. The modified surface of the inner core microcapsules increases its adhesion properties, which are suitable for the next layer formation at this step.

In step (g), a wall-forming polymer-plasticizer material for the next polymeric layer (herein designated "polymer-plasticizer shell") is prepared by dissolving or dispersing the same wall-forming polymer(s) of step (a) or different wall-forming polymer(s) with a plasticizer (the same or different as defined above in step (a)) in an organic solvent partially miscible with water such as ethyl acetate or its mixture with ethanol. At this stage, an anti-oxidant may be added to the polymer-plasticizer solution.

In an alternative, in step (g), a wall-forming polymer-mineral material for the next polymeric layer (herein designated "polymer-mineral shell") is prepared by dissolving or dispersing the same wall-forming polymer(s) of step (a) or different wall-forming polymer(s) with at least one mineral that is compatible with the method such as $\alpha$-modification of boron nitride, magnesium silicate, potassium, sodium, magnesium hydroalumosilicate, mica (and) magnesium myristate, or preferably, titanium dioxide in any of its mineral forms anatase, rutile, brookite or a mixture thereof, or titanium dioxide (and) magnesium myristate, in an organic solvent as defined above. Before addition of the mineral, a plasticizer and/or an emulsifier such as Tween-80 can be added to the polymer solution.

Step (h) is a repetition of step (b), in which an aqueous continuous phase is saturated by the same organic solvent (or mixture of solvents) used in step (g) and an appropriate emulsifier, e.g., PVA, is added to the aqueous phase.

Step (i) is a repetition of step (c), in which the polymer-plasticizer solution or polymer-mineral dispersion obtained in step (g) is poured into the aqueous continuous phase of step (h), under agitation, in the presence of an emulsifier (and an antioxidant, if the active ingredient is sensitive to oxidation), to form a polymer-plasticizer emulsion or polymer-mineral suspo-emulsion, respectively.

In step (j), the powdered cores microcapsules of step (f) are immersed in the polymer-plasticizer emulsion or polymer-mineral suspo-emulsion of step (i), thus forming a multi-component emulsion or a new suspo-emulsion, respectively, whereby a formation of "embryo" shells around the core microcapsules is initiated.

In step (k), while stirring, either an excess amount of water is added to the multi-component emulsion or to the new suspo-emulsion obtained in the previous step, or the multi-component emulsion or the new suspo-emulsion is poured into water, optionally containing an emulsifier, preferably PVA, for extraction of the organic solvent from said multi-component emulsion or suspo-emulsion. Preferably, the quantity of water is 10-30 folds compared to the whole quantity of organic solvent. This step is carried out under stirring and incubation for extraction of the solvent and formation of the microcapsules by conversion of the "embryo" shell into a solid polymer wall around the core microcapsule, thus obtaining double-layer microcapsules. The incubation period depends on the desirable size of microcapsules to be obtained.

The double-layer microcapsules are then immersed in an aqueous solution of ethanol (as in step (e) above), in order to remove residual amounts of the organic solvent, separated from the water, e.g., by sedimentation, filtration or centrifugation, and dried. Prior to drying, if desired, the microcapsules may be washed with water and/or water-ethanol solution again in order to remove traces of solvent. For this purpose, the final microcapsules after filtration are immersed in an aqueous solution of 5% ethanol for a period of 2-12 hours.

In this way, double-layer microcapsules are obtained. If additional layers are desired, these microcapsules are subjected to a specific surface treatment aimed to increase the polymer adhesion and then additionally coated with one or more outer shells, as described in steps (f) to (l). The outer shell typically has a less porous and smoother spherical surface as compared to the core single-layer microcapsules, and therefore it provides a better protection for the encapsulated active substance. This system enables a controlled release of the encapsulated agent only upon pressing and rubbing the microcapsule on the skin, scalp, teeth or gums.

According to the present invention, the active ingredient to be encapsulated may be an agent having biological activity, an odor agent or a color agent.

The agent having biological activity may be selected from vitamins, natural extracts, individual compounds isolated from natural sources, essential oils, and pharmaceutical agents for topical applications.

The vitamins that can be encapsulated according to the invention include the vitamins A, B, C, D, E, F, K, P, or mixtures thereof.

In one embodiment, the vitamin is vitamin A, either in its free form as Retinol or in its ester form as Retinol Palmitate. The most useable form of the vitamin is Retinol, the active form in the body. Retinol is an anti-oxidant vitamin used as nutritional factor and also as an active ingredient of topical/dental products. The activity of one IU (International Unit) of vitamin $A_1$ (equivalent to a USP unit) is 0.3 μg of all-trans Retinol. Retinol can be used for topical treatment of *Ichthyosis vulgaris* (an inherited skin disorder characterized by cornification of the skin) and common acne, and in anti-aging and rejuvenation formulations. However, Retinol (an unsaturated alcohol) is a small and unstable molecule and undergo chemical degradation/oxidation due to its high potential for chemical reactions with other molecules and should be stabilized before using it as an active ingredient in compositions. In order to enjoy the beneficial effects of Retinol and meet the shelf-life needed for topical/dental compositions, this active principle should be protected from oxidation. Encapsulation of Retinol by the single- or double-layered encapsulation method of the invention with an appropriate shell provides an effective solution for its stabilization and protection. The Retinol microcapsules of the invention are highly compatible with all types of topical/dental formulations and can be used in various applications including, without limiting, dental products, anti-aging products (creams, lotions, serums and masks), skin regeneration formulations, nourishing and moisturizing creams and anti-acne products.

In another embodiment, the vitamin is vitamin C (ascorbic acid), used in recent years as an active ingredient of cosmetics. Due to its antioxidant properties, it is considered to confer both antioxidant and photoprotection to skin against free radical attack and UV ray damage. However, Vitamin C is easily oxidized and, upon storage, exposure to light, oxygen, moisture and/or high temperature, undergoes rapid degradation. It is unstable in aqueous solution, even under neutral pH and at room temperature. The microencapsulation of Vitamin C according to the present invention permits its use as active ingredient in cosmetic composition for use as moisturizing cream, anti-aging cream, anti-wrinkle cream, sunscreen cream, and for stimulating collagen production.

In another embodiment, the vitamin is vitamin E, preferably as α-tocopherol. Tocopherols (Vitamin E) are well-known for their antioxidant properties making vitamin E one of the most widely consumed vitamins. However, vitamin E in its ester form (e.g., tocopherol acetate) is only effective as antioxidant to the formulation, but not to the skin. To be effective as antioxidant to the skin, α-tocopherol has to be used, but it is inherently unstable. The microcapsules of the invention preferably contain stable 25±1% α-tocopherol, and can be used in various types of cosmetic formulations such as sunscreen products, shampoos, conditioners, hair gels, liquid make-up and make-up tissue remover, and release about 95-97% of Vitamin E directly onto the skin/scalp upon application.

In a further embodiment, the vitamin is vitamin F, a mixture of unsaturated fatty acids essential for skin health and functionality, also known as Essential Fatty Acids (EFA; linoleic acid and alpha-linolenic acid.). Vitamin F oxidizes rapidly when incorporated in cosmetic formulation. The microencapsulation according to the invention offers a stable, active and odorless system of Vitamin F suitable for incorporation into moisturizing creams, anti-aging agents and anti-dryness serums. The microcapsules of the invention preferably contain stable 14±o.2% linolenic and linoleic free fatty acids α-tocopherol In another embodiment, the vitamin is Rutin (quercetin-3-rutinoside or vitamin P1), one of the most active natural flavonoids, highly effective as an antioxidant and free radical scavenger and in the treatment of cellulite due to its ability to control cross-linking of collagen synthesis. Rutin is widely applied in dermatological and cosmetic products due to its beneficial effects on the appearance of healthy skin and is well known for its potent antioxidant and anti-inflammatory properties and ability to strengthen and modulate the permeability of the walls of the blood vessels including capillaries. However, when incorporated into cosmetic formulations in its non-encapsulated form, Rutin tends to react with other ingredients and oxidizes quickly, resulting in change of the original color of the formulation and loss of its original biological activity. In order to maintain its potent biological activity and prevent its oxidation in cosmetic formulations, Rutin should be stabilized. The Rutin microcapsules of the present invention, developed specifically for topical application in order to stabilize the Rutin, preferably contain a high concentration (about 7%) of pure Rutin Hydrate from plant source.

In another embodiment of the present invention, the active ingredient having biological activity is a natural extract. In cosmetics, a natural extract is assumed to mean ingredients of botanical origin. To be truly natural it must be extracted from the relevant part of the plant without undergoing any significant chemical change. This definition includes plant oils. Any herbal extract or plant oil used for topical application, for example in the cosmetic industry, can be used according to the invention, but preferred herbal extracts and plant oils for encapsulation according to the invention include Licorice root extract, Grape Seed extract, Borage oil, Evening Primrose oil and Hippophae oil.

In one preferred embodiment of the invention, the natural extract is Grape Seed extract (GSE). GSE contains a high content of proanthocyanidins (also known as Oligomeric Proanthocyanidin Complexes or OPCs), a class of nutrients that belong to the flavonoid family and are potent antioxidants and free radical scavengers, reducing the harmful effects of UV radiation. In topical use, a great advantage of OPCs is a substantial increase in blood circulation at the sub-epitopical level and an improvement of intracellular membrane exchange of micronutrients. The proanthocyanidins (OPCs), however, are not stable and oxidize rapidly due to temperature and light influence or cross-reactions with other ingredients of topical formulation. The brown color developed in the final product is a result of OPCs oxidation. Encapsulation of GSE according to the present invention prevents oxidative degradation and brown color development, since the polymeric microcapsule walls prevent interaction of Grape Seed extract with other ingredients of the formulation, as well as guarantees the maximum release of OPCs from capsules on the skin upon application with maximum biological affect. The microcapsules of the present invention contain natural GSE rich in proanthocyanidins (min. 95% OPC), preferably about 6% GSE, have a uniform spherical shape with an average size of about 40 microns, and increase the stability and shelf-life of the OPCs, maintain its original activity, and prevents the oxidation and color development in the cosmetic formulation.

They are thus indicated as an active ingredient for incorporation in anti-aging creams, in after-sun creams for reduction of skin erythema, in moisturizing and revitalizing products, and in facial sunscreens for prevention of UV-induced lipid oxidation in skin.

In another preferred embodiment, the natural extract is Licorice root extract rich in Glabridin, a flavanoid known for its beneficial effects on the skin due to its anti-inflammatory and antioxidant properties. In addition, Glabridin has whitening/lightening and anti-spot properties, probably due to inhibition of tyrosinase and melanin synthesis. However, this extract tends to oxidize easily, resulting in a loss of Glabridin's original whitening activity. Moreover, Glabridin, as a flavanoid, is sensitive to pH changes and this factor is the reason for extreme instability of Glabridin in topical formulations, resulting in loss of its original activity and in the development of a dark brown color in formulations. The microcapsules of the present invention contain Licorice root extract rich in Glabridin. The product is standardized by a content of 4% Glabridin, which is protected by the microcapsules. These microcapsules provide stable lightening/whitening agent, prevent oxidation of the Glabridin, thereby guaranteeing original activity of Glabridin and providing a longer shelf life of the end product; prevent development of brown color in formulations; are highly stable in a wide pH range; are freely dispersible in all types of cosmetic formulations; and provide a unique control release of the extract only upon application onto the skin. The Licorice Extract microcapsules of the invention are, therefore, indicated as an active ingredient in whitening creams and lotions, age-defying creams and serums, anti-spots treatment formulations and lightening hand creams.

In another embodiment, the natural extract is Borage oil, rich in essential fatty acids such as linoleic acid, gamma-linolenic acid (GLA), oleic acid and others, in their triglyceride form, and one of the most concentrated natural forms of GLA. Borage oil is not stable and its active components undergo degradation. The microcapsules of the invention contain about 25% odorless encapsulated Borage oil with increased stability and shelf-life, maintain the GLA in its non-degraded active form, prevent development of distinct malodor during storage of the product, prevent skin irritation, and afford controlled release of high percentage of Borage oil directly to the skin. These microcapsules are indicated as an active ingredient for incorporation in moisturizing creams (especially for dry skin), anti-aging creams, repair formulations, hand creams, and lip-gloss and lip-protecting products.

In another embodiment, the natural extract is Evening Primrose oil (EPO), rich in essential fatty acids such as linoleic acid, gamma-linolenic acid (GLA), oleic acid and others, in their triglyceride form. EPO is not stable and its active components undergo degradation. The microcapsules of the invention contain about 25% odorless encapsulated EPO with increased stability and shelf-life, maintain the GLA in its non-degraded active form, prevent development of distinct malodor during storage of the product, prevent skin irritation, and afford controlled release of high percentage of EPO directly to the skin. These microcapsules are indicated as an active ingredient for incorporation in moisturizing creams (especially for dry skin), anti-wrinkle formulations, repair formulations, hand creams, whitening products, lip-gloss and and lip-protecting products.

In another embodiment, the natural extract is Sea Buckthorn (*Hippophae rhamnoides*) oil. This oil contains a unique mix of functional ingredients including a high concentration of carotenoids, palmitoleic acid, sito-sterols and derivatives of vitamins A and E, and is not stable. The microcapsules of the invention contain about 25% encapsulated natural Hippophae oil with increased stability and are indicated for incorporation as an active ingredient in anti-aging products, skin treatment formulations, e.g. after peeling, shaving, burns, etc., sunscreen products, eye-zone formulations, and after-sun products.

In a further embodiment of the invention, the active substance to be encapsulated is an individual compound isolated from a natural source such as, but not limited to, a coumarin, a chalcone or a flavonoid selected from the group consisting of flavans, flavanols, flavonols, flavones, flavanones, isoflavones, anthocyanidins, and proanthocyanidins.

It should be understood that an active ingredient used in the present invention may belong to more than one category as defined herein. Thus, Rutin, defined above as Vitamin P, is a flavonoid, as well Glabridin of the Licorice root extract and the proanthocyanidins of the Grape Seed extract.

In a further embodiment of the invention, the active substance to be encapsulated is an essential oil. Essential oils are a class of volatile oils extracted from plants, fruits or flowers by steam, distillation or solvent extraction. Examples of essential oils that can be encapsulated according to the invention include Basil Essential Oil, Eucalyptus Essential Oil, Geranium Essential Oil, Grapefruit Essential Oil, Lemon Essential Oil, Peppermint Essential Oil, Tea Tree oil, or mixtures thereof.

In one preferred embodiment, the essential oil is Tea Tree oil, an essential oil with a fresh camphoraceous odor, extracted from the leaves of the tree *Melaleuca alternifolia*. The oil has anti-inflammatory, antibacterial, antifungal, antiviral and antiparasitic properties. Tea Tree oil is beneficial in softening, regenerating and purifying the skin and scalp, in healing burns, disinfecting wounds and for treating spots and insect stings and bites. It is effective against fungal infections such as candidiasis, vaginal infections, fungal nail infections and for hemorrhoids. As a bath additive it may control bacteria in spas and pools. It is also known to reduce hypertrophic scarring and dandruff hair. Tea Tree Oil components include 1-terpinen-ol, responsible for most of the antimicrobial actions, 1,8-cineole, gamma terpinene, p-cymene and other terpenes. Tea Tree Oil is not stable and oxidizes and loses its original activity when incorporated in cosmetic formulations in its naked form, may cause skin irritation and has a very strong original odor due to its volatility. The microcapsules of the invention contain about 5% odorless encapsulated Tea Tree Oil with increased stability and shelf-life, preventing oxidation of unstable compounds and development of Tea Tree Oil's strong malodor in the formulation, and afford controlled release of high percentage of Tea Tree Oil directly to the skin/scalp. These microcapsules are indicated as an active ingredient for incorporation in facial care formulations for sensitive and delicate skin, personal hygiene products and shampoos for damaged and delicate hair, and anti-dandruff shampoos.

In an additional embodiment of the invention, the active ingredient to be encapsulated is a pharmaceutical agent for topical applications, e.g. an antibiotic such as, but not limited to, a macrolide antibiotic selected from Erythromycin, Azithromycin or Clarithromycin. Clarithromycin is a semi-synthetic macrolide antibiotic used to treat certain infections caused by bacteria, such as pneumonia, bronchitis, and infections of the ears, lungs, sinuses, skin, and throat. It also is used to prevent disseminated Mycobacterium avium complex (MAC) infection in patients with human immunodeficiency virus (HIV). Clarithromycin is used orally, but expanding its use for topical application opens new possibilities for administration of this highly potent antibacterial agent with less tolerated drugs such as the tretinoins. Clarithromycin, as many other antibiotics, is very sensitive to degradation due to hydrolysis in water-containing formulations. The Clarithromycin microcapsules of the present invention are specifically developed for topical use and protect the antibiotic from degradation once used in water-containing formulations.

In another embodiment of the invention, the active ingredient to be encapsulated is an odor (usually a pleasant odor) agent selected from the group consisting of fragrances, perfumes, essential oils and compounds extracted therefrom, and volatile natural and synthetic compounds. These agents can be used to impart a pleasant odor to the cosmetic formulation and/or to mask an undesired odor of other components of the formulation.

Agents with odor properties are widely used in topical products. Typically, these agents such as fragrances, perfumes and other volatile materials suffer from instability under specific conditions such as pH of the formulation or they crossreact with other ingredients of the formulation. For these reasons, it is necessary to encapsulate this type of ingredients. The microcapsules of the invention containing a fragrance have been developed specifically in order to solve the above-mentioned problems.

In one preferred embodiment, the volatile compound is Menthol, a monocyclic terpene alcohol obtained from peppermint oil or other mint oils, or prepared synthetically by hydrogenation of thymol. Menthol is a white crystal with a characteristic refreshing mint odor, which provides cosmetic formulations with a fresh sensation, cooling effect, calming qualities and short-term relief. However, Menthol, as a volatile ingredient, has a tendency to evaporate and to change the original content/odor of the formulation. In addition, it is difficult to disperse Menthol homogeneously in cosmetic formulations and usually requires predispersion with ethanol. The precipitation of Menthol from the formulations, its original strong characteristic odor and its potential cross-linking with other ingredients, are reasons that difficult its use in topical/dental products. The odorless Menthol microcapsules of the present invention contain about 10% Menthol. They protect the Menthol from oxidation and maintain its original activity after incorporation into cosmetic formulations. They mask Menthol's characteristic odor while maintaining the original smell, preventing it from reacting with other ingredients in the formulation and providing a long lasting sensation/cooling effect upon application on skin. The microcapsules are homogeneously dispersed in cosmetic formulations without requiring the use of alcohol and are, therefore, indicated as an ingredient for oral hygiene care, e.g. toothpastes, mouth rinses, sun-screen products, cooling after-sun lotions, calming creams and refreshing pre- and after-shave products.

In an additional embodiment of the invention, the active ingredient to be encapsulated is a color agent selected from the group consisting of organic and inorganic pigments, colorants and color agents from natural source.

The color agents that can be used according to the invention include the pigments Carmine, Iron Oxides, Titanium dioxide, and Chrome Oxide/Hydroxide, the colorants D&C Red 21 Aluminum Lake, D&C Red 7 Calcium Lake, D&C Green 6 Liposoluble, and Aluminium Blue #1 (Indigo Carmine Lake). In one preferred embodiment, the pigment is Titanium dioxide (used to lighten other pigments and to lend opacity to formulations) in any one of its mineral forms anatase, brookite or rutile, or mixtures thereof. In another preferred embodiment, the color agent is Iron Oxides, the most widely used of the inorganic pigments, in any of the 3 basic colors—red, black and yellow iron oxides, or mixtures thereof. From these 3 oxides and the addition of Titanium dioxide, any shade of brown (skin tones) can be achieved.

In the method of the invention, the polymer shell of the multi-layer microcapsules may be a polymer-plasticizer or polymer-mineral shell.

In one embodiment, the inner and outer polymer shells are both polymer-plasticizer shells and the polymer of the inner core microcapsule and of the outer shells may be identical or different.

In another embodiment, the inner and outer polymer shells are both polymer-mineral shells and the polymer of the inner core microcapsule and of the outer shells may be identical or different.

In a further embodiment, the inner polymer shell is a polymer-plasticizer shell and the outer polymer shell is a polymer-mineral shell or the inner polymer shell is a polymer-mineral shell and the outer polymer shell is a polymer-plasticizer shell and the polymers of both shells may be identical or different.

In preferred embodiments, the wall-forming polymer is ethyl cellulose, poly(methyl methacrylate)-co-(methacrylic acid) (1:0.16), poly(ethyl acrylate)-co-(methyl methacrylate)-co-(trimethylammonium-ethyl methacrylate chloride) (1:2:0.1), or a mixture thereof.

In preferred embodiments, the method of the invention is used for the preparation of double-layer and triple-layer microcapsules.

The present invention further provides multi-layer microcapsules for topical application, consisting of an inner core microcapsule which contains an active ingredient located within a wall-forming polymer, and one or more outer shells of the same or different wall-forming polymer coating the inner core microcapsule, wherein said multi-layer microcapsules are obtained according to the method of the invention.

The multi-layer, including the double- and triple-layer, microcapsules according to the invention have an outer diameter of the inner core microcapsule in the range of 1-100 µm and an outer diameter of the multi-layer microcapsule in the range of 10-200 µm, preferably 30-50 µm.

The present invention further provides double-layer microcapsules for topical application, consisting of an inner core microcapsule which contains an active ingredient located within a wall-forming polymer, and one outer shell of the same or different wall-forming polymer coating the inner core microcapsule, wherein said double-layer microcapsules are obtained according to the method of the invention. It should be understood that the active ingredients of the double-layer microcapsules are the same as defined above for the method of the invention In a preferred embodiment, the polymer shells of the double-layer microcapsules are a polymer-plasticizer and/or polymer-mineral shell.

In one embodiment, the inner and outer polymer shells of the double-layer microcapsules are both polymer-plasticizer shells and the polymer of the inner core microcapsule and of the outer shells may be identical or different.

In another embodiment, the inner and outer polymer shells of the double-layer microcapsules are both polymer-mineral shells and the polymer of the inner core microcapsule and of the outer shells may be identical or different.

In another embodiment, the inner polymer shell of the double-layer microcapsules is a polymer-plasticizer shell and the outer polymer shell is a polymer-mineral shell or the inner polymer shell is a polymer-mineral shell and the outer polymer shell is a polymer-plasticizer shell and the polymers of both shells may be identical or different.

In preferred embodiments, the wall-forming polymers used in the double-layer microcapsules are ethyl cellulose, poly(methyl methacrylate)-co-(methacrylic acid) (1:0.16), poly(ethyl acrylate)-co-(methyl methacrylate)-co-(trimethyl-ammonium-ethyl methacrylate chloride) (1:2:0.1), or a mixture thereof; the plasticizer that forms the polymer-plasticizer shell is selected from the group consisting of tricaprylin, trilaurin, tripalmitin, triacetin, triethyl citrate, acetyltriethyl citrate, isopropyl myristate, paraffin oil, and mixtures thereof; and the mineral that forms the polymer-mineral shell is selected from the group consisting of titanium dioxide, boron nitride, magnesium silicate, potassium, sodium, magnesium hydroalumosilicate, mica (and) magnesium myristate, titanium dioxide (and) magnesium myristate, and mixtures thereof.

The active ingredient encapsulated within the double-layer microcapsules may consist of one or more than one active ingredient or said active ingredient may be in mixture with an additive, e.g. an antioxidant.

In one preferred embodiment, the double-layer microcapsules contain an active ingredient selected from Retinol, Retinol Palmitate, Licorice Extract, or Tea Tree Oil and the wall-forming polymer of the inner and outer polymer-plasticizer shells is poly(methyl methacrylate)-co-(methacrylic acid) (1:0.16).

In another preferred embodiment, the active ingredient is Rutin and the wall-forming polymer of the inner and outer polymer-plasticizer shells is a mixture of poly(methyl methacrylate)-co-(methacrylic acid) (1:0.16) and poly(ethyl acrylate)-co-(methyl methacrylate)-co-(trimethylammonium-ethyl methacrylate chloride) (1:2:0.1).

In another preferred embodiment, the double-layer microcapsules contain an active ingredient selected from Grape Seed Extract or Iron oxide pigments, and the wall-forming polymer of the inner polymer-mineral shell and of the outer polymer-plasticizer shell is poly(ethyl acrylate)-co-(methyl methacrylate)-co-(trimethyl-ammonium-ethyl methacrylate chloride) (1:2:0.1).

In another preferred embodiment, the double-layer microcapsules contain as active ingredient Menthol and the wall-forming polymer of the inner polymer-plasticizer shell and of the outer polymer-mineral shell is poly(methyl methacrylate)-co-(methacrylic acid) (1:0.16).

In another preferred embodiment, the double-layer microcapsules contain an active ingredient selected from Chrome oxide/hydroxide pigment or D&C Red Calcium Lake and the wall-forming polymer of the inner polymer-plasticizer shell and of the outer polymer-mineral shell is poly(ethyl acrylate)-co-(methyl methacrylate)-co-(trimethyl-ammonium-ethyl methacrylate chloride) (1:2:0.1).

In another preferred embodiment, the double-layer microcapsules contain an active ingredient selected from. Retinol, Carmine pigment, D&C Red 21 Aluminum Lake or D&C Green 6 Liposoluble, and the wall-forming polymer of the inner polymer-plasticizer shell is poly(methyl methacrylate)-co-(methacrylic acid) (1:0.16) and of the outer polymer-mineral shell is poly(ethyl acrylate)-co-(methyl methacrylate)-co-(trimethyl-ammonium-ethyl methacrylate chloride) (1:2:0.1).

In another preferred embodiment, triple-layer microcapsules are provided wherein the active ingredient is Aluminum Blue #1, the wall-forming polymer of the inner polymer-plasticizer shell is a mixture of poly(methyl methacrylate)-co-(methacrylic acid) (1:0.16) and poly(ethyl acrylate)-co-(methyl methacrylate)-co-(trimethyl-ammonium-ethyl methacrylate chloride) (1:2:0.1), and of the two outer polymer-mineral shells is poly(ethyl acrylate)-co-(methyl methacrylate)-co-(trimethyl-ammonium-ethyl methacrylate chloride) (1:2:0.1).

The present invention affords the production of uniform microcapsules containing a high loading of the active ingredients. The microcapsules are spherical in shape and are suitable, among many other applications, for cosmetic, dermatological, baby care and oral hygiene applications. The microcapsules can be effectively used in topical applications due to the unique ability of the capsules' walls to soften upon rubbing or pressing, e.g. onto the skin or scalp, when used topically, thereby releasing 95-97% of the active ingredient onto the target area. The active ingredient remains stable during the whole preparation method and also in the process of its incorporation into compositions and during storage. The multi-layer microcapsules of the invention are impermeable to outer materials, breakable upon pressing and rubbing and composed of materials that do not react with or modify the encapsulated active principle.

The present invention further relates to composition for topical application comprising single-layer microcapsules obtained by the method of the invention, wherein the active ingredient is a macrolide antibiotic selected from the group consisting of Erythromycin, Clarithromycin and Azithromycin, or such compositions for oral hygiene.

The present invention also relates to compositions for topical application comprising multi-layer, particularly double-layer, microcapsules obtained by the method of the invention In one embodiment, the invention provides compositions comprising said double-layer microcapsules for skin care, skin supplement, hair care, sun care, and baby care oral hygiene, and oral care.

In another embodiment, the invention provides compositions comprising double-layer microcapsules for oral hygiene and oral care.

In another embodiment, the invention provides compositions comprising double-layer microcapsules for topical application, wherein the active ingredient is a pharmaceutical.

The invention will now be illustrated by the following non-limiting Examples.

EXAMPLES

Example 1

A Process for Encapsulation of Oil

An aqueous phase was prepared as follows: 0.5 g of sodium lauryl sulfate was dissolved in 50 ml of tap water saturated with 6 ml of ethyl acetate. An organic phase was prepared by dissolving 0.7 g oil and 0.3 g ethyl cellulose in 5 ml of ethyl acetate. The resulting organic phase was poured into the aqueous phase while stirring and then 100 ml of fresh water were added. After microcapsules were formed during a period of about 3-10 minutes, they were filtered, washed by water and dried at the temperature no higher 20° C. An average diameter of the microcapsules was 70 μm. Efficiency of encapsulation reached was 99%.

In this way, oils such as Tea Tree Oil, Evening Primrose Oil, Borage Oil and Hippophae Oil, that suffer from a lack of stability due to degradation of its active principles, have been successfully microencapsulated, resulting in microcapsules with increased stability and shelf-life of the oil, preventing development of distinct malodor during the storage of the product, affording controlled release of the oil only upon dermal application, and delivering high percentage of the oil directly to the skin.

Example 2

A Process for Encapsulation of Vitamin F

An aqueous phase was prepared as in Example 1. The pH of the aqueous phase was further adjusted to 3 by citric acid. An organic phase was prepared by dissolving 0.25 g vitamin F in a mixture of natural triglycerides of fatty acids, 0.01 g antioxidant that can be chosen from butylated hydroxyanisole (BHA), butylated hydroxytoluene (BHT) or tocopherol (vitamin E) and 0.74 g poly (methyl) methacrylate (PMMA) in 5 ml of ethyl acetate.

The resulting organic phase was poured into the aqueous phase while stirring and then 100 ml of fresh water were added. The resulting microcapsules formed were filtered, washed by water and dried at the temperature no higher than 20° C. An average diameter of the microcapsules was 50 µm.

Example 3

A Process for Encapsulation of Vitamin E

The preparations of the aqueous and organic phases were done in the same manner as in Example 2, vitamin E (Tocopherol) rather than vitamin F being dissolved in the organic phase. The resulting organic phase was poured into the aqueous phase while stirring and then 100 ml of fresh water were added. The resulting microcapsules formed were filtered, washed by water and dried at a temperature no higher 20° C. An average diameter of the microcapsules was 40 µm.

Example 4

A Process for Encapsulation of Vitamin A Palmitate

An aqueous phase was prepared by dissolving 0.5 g of poly (vinyl alcohol) in 50 ml water saturated by 6 ml of ethyl acetate. An organic phase was prepared by dissolving 0.075 g Retinol Palmitate, 0.1 g mineral oil, 0.01 g of an antioxidant (chosen from BHA, BHT, tocopherol or their mixture) and 0.815 g PMMA in 5 ml of ethyl acetate. The organic phase was poured into the aqueous phase while stirring and then 100 ml of fresh water were added. The microcapsules formed were filtered, washed by water and dried at the temperature no higher 20° C. An average diameter of the microcapsules was 40 µm.

Example 5

A Process for Encapsulating a Suspension of Vitamin C

An aqueous phase was prepared by saturating 100 ml water containing 0.08% sodium lauryl sulphate by 12 ml ethyl acetate. Separately an organic phase was prepared by adding 0.5 g of finely grounded vitamin C (particle size 5-10 micron) to a solution of 2g PMMA in 10 ml ethyl acetate. After the addition, the batch was dispersed by sonication. Organic phase was poured into the aqueous phase, and homogenized. Then, 400 ml of fresh water containing 0.08% sodium lauryl sulphate were added for the extraction of the ethyl acetate and mixing was continued for several min. The formed microcapsules were separated by sedimentation, washed by water and dried.

Example 6

A Process for Encapsulation of a Mixture of Vitamins A and E

An organic phase was prepared as follows: 0.075 g vitamin A Palmitate, 0.25 g of vitamin E and 0.675 g of PMMA were dissolved in ethyl acetate. An aqueous phase was prepared as described in example 17. Then mixing of phases, dilution by water, formation of microcapsules and their isolation was carried as described in Example 4.

Example 7

Encapsulation of Retinol Palmitate (Vitamin A) into Single-Layered Microcapsules with an Outer Polymer-Plasticizer Shell Encapsulation of Retinol Palmitate into single-layered microcapsules for oral hygiene application, was carried out according to the following procedure.

At the first stage, the microcapsules containing Retinol Palmitate were prepared by adding 3 g Retinol Palmitate (BASF), 1 g antioxidant (chosen from BHA, BHT or a mixture thereof), 6 g plasticizer (chosen from triacetin, triethyl citrate, acetyltriethyl citrate or a mixture thereof) to 10 g Ethylcellulose N7 (Hercules Inc.) solution in 140 ml ethyl acetate. The solution was poured, while stirring, into aqueous solution prepared by saturation of 360 ml water containing 2 g PVA with 40 ml ethyl acetate. The obtained emulsion was poured into 4.5 L water containing 2 g PVA, while stirring, and incubated for a period of 3-10 min at 20° C. to extract ethyl acetate and microcapsules formation. Upon the gradual removal of the organic solvent, a solid polymer shell is formed surrounding the droplets of emulsion, enveloping all ingredients (active, antioxidant, plasticizer), which are insoluble in obtained solvent system (water with trace of organic solvent), inside of the formed solid core microcapsules. The formed microcapsules were separated by sedimentation, washed with 10% aqueous solution of ethanol, and dried at a temperature not higher than 20° C. to obtain a free flowing powder. The outer diameter of the obtained microcapsules was in the range of 20-50 µm.

Example 8

Encapsulation of Tocopherol (Vitamin E) into Single-Layered Microcapsules with an Outer Polymer-Plasticizer Shell Encapsulation of Tocopherol into single-layered microcapsules for oral hygiene application, was carried out according to the following procedure:

At the first stage, the microcapsules containing Tocopherol were prepared by adding 6 g DL-α-Tocopherol (BASF), 1 g antioxidant (chosen from BHA, BHT or a mixture thereof), 4 g plasticizer (chosen from triacetin, triethyl citrate, acetyltriethyl citrate or a mixture thereof) to 9 g of Ethylcellulose N7 (Hercules Inc.) solution in 120 ml ethyl acetate. The solution was poured, while stirring, into aqueous solution prepared by saturation of 300 ml water containing 1.5 g PVA with 40 ml ethyl acetate. The obtained emulsion was poured into 4 L water containing 2 g PVA, while stirring, and incubated for a period of 3-10 min at 20° C. to extract ethyl acetate and microcapsules formation. The obtained microcapsules were separated by sedimentation, washed with 10% aqueous solution of ethanol, and dried at a temperature not higher than 20°

C., to obtain a free flowing powder. The outer diameter of the obtained microcapsules was in the range of 20-50 μm.

Example 9

Encapsulation of Natural Sea Buckthorn Oil (*Hippophae Rhamnoides*) Oil into Single-Layered Microcapsules with an Outer Polymer-Plasticizer Shell Encapsulation of Sea Buckthorn Oil (*Hippophae Rhamnoides*) into single-layered microcapsules for oral hygiene application, was carried out according to the following procedure:

At the first stage, the microcapsules containing Sea Buckthorn Oil were prepared by adding 5 g Sea Buckthorn Oil, 1 g of antioxidant (chosen from BHA, BHT or a mixture thereof), 3 g plasticizer (chosen from triacetin, triethyl citrate, acetyltriethyl citrate or a mixture thereof) to 11 g of Ethylcellulose N7 (Hercules Inc.) solution in 120 ml ethyl acetate. The solution was poured, while stirring, into aqueous solution prepared by saturation of 300 ml water containing 1.5 g PVA with 35 ml ethyl acetate. The obtained emulsion was poured into 4 L water containing 2 g PVA, while stirring, and incubated for a period of 3-10 min at 20° C. to extract ethyl acetate and microcapsules formation. The obtained microcapsules were separated by sedimentation and isolated as described in Example 8. The outer diameter of the obtained microcapsules was in the range of 20-50 μm.

Example 10

Encapsulation of Natural Tea Tree Oil (*Melaleuca Alternifolia*) into Single-Layered Microcapsules with an Outer Polymer-Plasticizer Shell Encapsulation of Tea Tree Oil (*Melaleuca Alternifolia*) into single-layered microcapsules for oral hygiene application, was carried out according to the following procedure:

At the first stage, the microcapsules containing Tea Tree Oil were prepared by adding 5 g Tea Tree Oil (Bronson and Jacobs), 1 g antioxidant (chosen from BHA, BHT or a mixture thereof), 4 g plasticizer (chosen from triacetin, triethyl citrate, acetyltriethyl citrate or a mixture thereof) to 10 g Ethylcellulose N7 (Hercules Inc.) solution in 140 ml ethyl acetate. The solution was poured, while stirring, into aqueous solution prepared by saturation of 360 ml water containing 2 g PVA with 40 ml ethyl acetate. The obtained emulsion was poured into 4.5 L of water containing 2 g PVA, while stirring, and incubated for a period of 3-10 min at 20° C. to extract ethyl acetate and microcapsules formation. The obtained microcapsules were separated by sedimentation and isolated as described in Example 8. The outer diameter of the obtained microcapsules was in the range of 20-50 μm.

Example 11

Encapsulation of a Fragrance into Single-Layered Microcapsules with an Outer Polymer-Plasticizer Shell Encapsulation of a fragrance into single-layered microcapsules, was carried out according to the following procedure:

The microcapsules containing fragrance were prepared by adding 8 g of fragrance (Topnote UN, Firmenich), 2 g plasticizer (chosen from trilaurin, tricaprylin, tripalmitin or a mixture thereof) to a solution of 10 g poly(methyl methacrylate)-co-(methacrylic acid) (1:0.16) in 60 ml ethyl acetate while stirring. This solution was poured, while stirring, into aqueous solution prepared by saturating 200 ml distilled water containing 0.5 g PVA with 25 ml ethyl acetate. The obtained emulsion was poured into 2 L of distilled water containing 0.1 g PVA, while stirring, and incubated for a period of 10-15 min at 20° C. for extraction of ethyl acetate and microcapsules formation. The formed microcapsules were separated by sedimentation, washed with 10% aqueous solution of ethanol and dried at a temperature not higher than 15° C. to get a free flowing powder. The outer diameter of the obtained microcapsules was in the range of 10-60 μm.

Example 12

Encapsulation of Antibiotic Clarithromycin into Single-Layered Microcapsules with an Outer Polymer-Plasticizer Shell Encapsulation of Clarithromycin into single-layered microcapsules was carried out according to the following procedure:

At the first stage, the microcapsules containing Clarithromycin were prepared by adding 4 g Clarithromycin (Zhejing Huangyan Biochemical Industry Co. Ltd) to 12 g Ethylcellulose N7 (Hercules Inc.) and 4 g Eudragit E 100 (cationic copolymer based on dimethylaminoethyl methacrylate and neutral methacrylic esters; Degussa) solution in 92 g ethyl acetate. The solution was poured, while stirring, into aqueous solution prepared by saturation of 300 ml water containing 1.5 g PVA with 35 ml ethyl acetate. The obtained emulsion was poured into 3.2 L water containing 1.5 g PVA, while stirring, and incubated for a period of 10-15 min at 20° C. for extraction of ethyl acetate and microcapsules formation. The formed microcapsules were separated by sedimentation, washed with 10% aqueous solution of ethanol and dried at a temperature not higher than 20° C. to get a free flowing powder. The outer diameter of the microcapsules was in the range of 30-60 μm.

Example 13

Encapsulation of Retinol (Vitamin A) into Double-Layered Microcapsules with Inner and Outer Polymer-Plasticizer Shells At the first stage, the inner core microcapsules containing Retinol coated with a polymer-plasticizer shell, were prepared by adding 3 g Retinol 50C (BASF), 1 g antioxidant (chosen from BHA, BHT or a mixture thereof) and 8 g plasticizer (chosen from trilaurin, tricaprylin, tripalmitin or a mixture thereof) to a solution of 8 g poly(methyl methacrylate)-co-(methacrylic acid) (1:0.16) in 57 g ethyl acetate, while stirring. This solution was poured, while stirring, into aqueous solution prepared by saturating 220 ml distilled water containing 0.5 g PVA, with 30 ml ethyl acetate. The obtained emulsion was poured into 2 L distilled water, while stirring, and incubated for a period of 10-15 min at 20° C. for extraction of ethyl acetate and microcapsules formation. The obtained core microcapsules were separated by sedimentation, washed with 10% aqueous solution of ethanol and dried at a temperature not higher than 20° C. to get a free flowing powder. The outer diameter of the microcapsules was in the range of 10-40 μm.

At the second stage, in order to treat the core surface before coating with an outer shell, 20 g of the inner core microcapsules were powdered with 2 g of dioxosilicon (Aerosil 200, Degussa AG). Specific surface areas (SSA) of the inner core microcapsules were determined before and after modification by the nitrogen absorption method [for detailed description of the nitrogen absorption method see: Santamarina, J. C., Klein, K. A., Wang, Y. H., Prencke, E. Specific surface: determination and relevance. *Can. Geotech. J.* 39, 233-241 (2002)]. The SSA values for cores before and after powdering were 0.93 and 2.78 $m^2/g$, respectively.

At the third stage, the powdered modified inner cores containing Retinol 50C were coated with an outer polymer-plasticizer shell. For this purpose, a polymer-plasticizer solution was prepared by dissolving 3 g poly(methyl methacrylate)-co-(methacrylic acid) [1:0.16] in 64 ml ethyl acetate while stirring for a period of 30 min at 40° C. The solution was cooled to room temperature, and 2 g of plasticizer (chosen from trilaurin, tricaprylin, tripalmitin or a mixture thereof), and 1 g of antioxidant (chosen from BHA, BHT or a mixture thereof) were dissolved therein. The resulting polymer-plasticizer solution was emulsified in 350 ml distilled water containing 2 g PVA, which was preliminarily saturated with 47 ml ethyl acetate, followed by addition of 20 g powdered modified inner cores, which were dispersed for a period of about 15 min to form a suspo-emulsion. The obtained multicomponent emulsion was poured into 3 L distilled of water, while stirring, and incubated for 10-15 min in order to extract ethyl acetate and allow formation of double-layered microcapsules. Separation and isolation of the double-layered microcapsules as a free flowing powder was performed as described in the first stage. The outer diameter of the obtained microcapsules was in the range of 40-90 μm.

Example 14

Encapsulation of Retinol (Vitamin A) into Composite Double-Layered Microcapsules with an Inner Polymer-Plasticizer Shell and an Outer Polymer-Mineral Shell At the first stage, the inner core microcapsules containing Retinol coated with a polymer-plasticizer shell, were prepared by adding 3 g Retinol 50C (BASF), 1 g antioxidant (chosen from BHA, BHT or a mixture thereof) and 7 g plasticizer (chosen from trilaurin, tricaprylin, tripalmitin or a mixture thereof) to a solution of 7 g poly(methyl methacrylate)-co-(methacrylic acid) (1:0.16) in 57 g ethyl acetate, while stirring. The solution was poured while stirring into aqueous solution prepared by saturating 220 ml distilled water containing 0.5 g PVA with 30 ml ethyl acetate. The obtained emulsion was poured in 2 L distilled of water, while stirring, and incubated for a period of 10-15 min at 20° C. for extraction of ethyl acetate and microcapsules formation. The obtained core microcapsules were isolated by sedimentation, washed with 10% aqueous solution of ethanol, dried at a temperature not higher than 20° C. to get a free flowing powder. The outer diameter of the microcapsules was in the range of 10-40 μm.

At the second stage, in order to treat the core surface before coating with an outer shell, 20 g of the core microcapsules were powdered with 2 g of dioxosilicon (Aerosil 200, Degussa AG).

At the third stage, powdered modified core microcapsules containing Retinol 50C were coated with an outer polymer-mineral shell. For this purpose, a polymer-mineral dispersion was prepared by dissolving 1 g Eudragit RS PO (poly(ethyl acrylate)-co-(methyl methacrylate)-co-(trimethylammonium-ethyl methacrylate chloride, 1:2:0.1; Degussa), 3 g triglyceride (chosen from trilaurin, tricaprylin, tripalmitin or a mixture thereof), 1 g antioxidant (chosen from BHA, BHT or a mixture thereof) in 52 ml ethyl acetate, while stirring at 40° C., followed by addition of 4 g titanium dioxide (chosen from anatase, rutile, brookite or a mixture thereof) and dispersion by ultrasonic for 3 min. Then, 20 g of powdered modified inner cores were added to the suspension and stirred. The obtained polymer-mineral dispersion was emulsified in 180 ml of distilled water containing 0.5 g PVA, which was preliminarily saturated with 22 ml ethyl acetate. This multicomponent suspo-emulsion was poured into 1 L of distilled water, while stirring, and incubated for 10 min for extraction of ethyl acetate and formation of the microcapsules. The isolation of the composite double-layered microcapsules as a free flowing powder was performed as described in stage one. The outer diameter of the obtained composite microcapsules was in the range of 40-80 μm, which is two-fold larger as compared to the diameter of the cores alone.

Figure 1B:
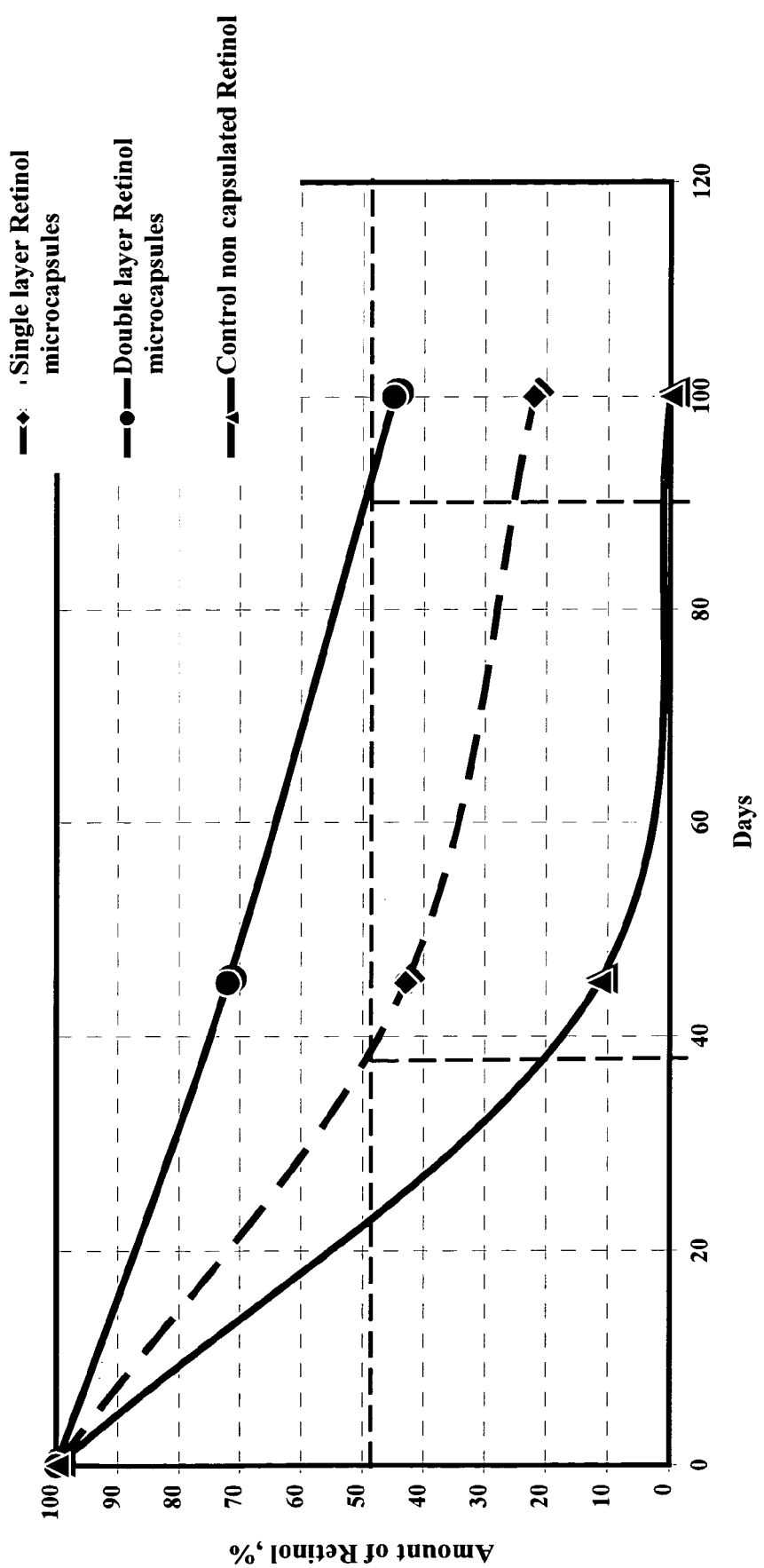

The efficacy of protection of Retinol from oxidation by single-layer and double-layer microcapsules was determined analytically in different model dermal formulations with incorporated Retinol single- and double-layer microcapsules, which were monitored by HPLC analyses in comparison with non-encapsulated Retinol, during stability tests at different temperature conditions. Measurements of oxidation kinetics were made at 25° C. (FIG. 1A) and at 40° C. (FIG. 1B). The results show that for the encapsulated Retinol in model gel formulation, 50% of oxidation of Retinol protected by composite double-layered microcapsules occurred after 90 and 500 days (responsive to temperature conditions) in comparison to Retinol protected by single-layered microcapsules that achieve the same level of oxidation after 38 and 220 days (responsive to temperature conditions). The concentration of the Retinol in the formulation was 4000IU/g.

Example 15

Encapsulation of Retinol Palmitate (Vitamin A) into Double-Layered Microcapsules with Inner and Outer Polymer-Plasticizer Shells At the first stage, the inner core microcapsules containing Retinol Palmitate were coated with a polymer-plasticizer shell were prepared by adding 3 g Retinol Palmitate (BASF), 1 g antioxidant (chosen from BHA, BHT or a mixture thereof), 6 g plasticizer (chosen from trilaurin, tricaprylin, or a mixture thereof) to 10 g of poly(methyl methacrylate)-co-(methacrylic acid) (1:0.16) solution in 60 g ethyl acetate. The solution was poured, while stirring, into aqueous solution prepared by saturation of 200 ml distilled water containing 1 g PVA, with 90 ml ethyl acetate. The obtained emulsion was poured into 3 L of distilled water containing 3 g PVA and incubated for 10-15 min for extraction of ethyl acetate and formation of cores. The obtained core microcapsules were isolated by sedimentation, washed with 10% aqueous solution of ethanol, dried at a temperature not higher than 20° C. to get a free flowing powder. The outer diameter of the obtained core microcapsules was in the range of 10-40 μm.

At the second stage, in order to prepare the core surface for coating with an outer shell, 20 g of the inner core microcapsules were powdered with 2 g dioxosilicon (Aerosil 200, Degussa AG).

At the third stage, the powdered modified inner cores containing Retinol Palmitate were coated with a second polymer-plasticizer shell. For this purpose, the polymer-plasticizer solution was prepared by dissolving 12 g of poly(methyl methacrylate)-co-(methacrylic acid) (1:0.16) in 60 ml ethyl acetate, while stirring for a period of 30 min, followed by dissolving a mixture of 7 g plasticizer (chosen from trilaurin, tricaprylin, tripalmitin or a mixture thereof) and 1 g antioxidant (chosen from BHA, BHT or a mixture thereof). The obtained polymer-plasticizer solution was emulsified in 300 ml of distilled water containing 1.5 g PVA, which was preliminarily saturated with 30 ml ethyl acetate, and 20 g of powdered cores were dispersed for a period of 15 min to form a suspo-emulsion. The resulting multi-component emulsion was poured into 2 L distilled water, while stirring, and the system was incubated for 10 min to allow extraction of ethyl acetate the formation of double-layered microcapsules. The procedure of isolation of the double-layered microcapsules as a free flowing powder was performed as described in the first stage. The outer diameter of the final double-layered microcapsules was in the range of 50-100 µm.

Example 16

Encapsulation of Natural Grape Seed Extract into Composite Double-Layered Microcapsules with an Inner Polymer-Mineral Shell and an Outer Polymer-Plasticizer Shell At the first stage, the inner core microcapsules containing Grape Seed extract (GSE) coated with a polymer-mineral shell, were prepared as follows: an organic dispersion was prepared separately by dispersing 10 g titanium dioxide (chosen from anatase, brookite, rutile or a mixture thereof) in 33 ml ethyl acetate for a period of 30 min, followed by addition of 2 g Eudragit RS PO (Degussa), 2 g GSE (AHD International, LLC), 1 g antioxidant (chosen from BHA, BHT or a mixture thereof), 4 g water and 5 g plasticizer (chosen from acetyl triethyl citrate, isopropyl myristate or a mixture thereof), while stirring. Afterwards, all the ingredients of the suspension were stirred for a period of 10 min and then poured into 200 ml of water containing 1 g PVA, which was preliminary saturated with 26 ml ethyl acetate, while stirring. The resulted dispersion was poured into 2 L of water, while stirring, and incubated for 3-5 min at 20° C., for extraction of ethyl acetate and formation of microcapsules. The formed microcapsules were separated by sedimentation, washed with water and dried at room temperature to get a free flowing powder. The outer diameter of the microcapsules obtained was in the range of 20-60 µm.

At the second stage, in order to prepare the core surface for coating with an outer shell, 20 g of the core microcapsules were powdered with 0.16 g dioxosilicon (Aerosil 200, Degussa AG).

At the third stage, the powdered modified cores containing GSE coated with a polymer-mineral shell were coated with a polymer-plasticizer shell according to the following procedure: 1 g Eudragit RS PO were dissolved in 20 ml ethyl acetate while stirring for a period of 5 min, followed by addition of 1 g plasticizer (chosen from trilaurin, tricaprylin, tripalmitin or a mixture thereof), 1 g of antioxidant (chosen from BHA, BHT or a mixture thereof). This polymer-plasticizer solution was emulsified in 170 ml of water containing 1 g PVA, which was saturated with 20 ml ethyl acetate beforehand. Then, 20 g of powdered modified inner cores were added to the emulsion and dispersed to form a suspo-emulsion. The resulting multi-component emulsion was poured into 2 L of water and incubated for a period of 15 min at 20° C. for extraction of ethyl acetate and microcapsule formation. The isolation of the obtained composite double-layered microcapsules as a free flowing powder was performed as described in stage one. The outer diameter of the composite microcapsules was in the range of 60-90 µm.

Example 17

Encapsulation of Licorice Root Extract (*Glycyrrhiza Glabra*) into Double-Layered Microcapsules with Inner and Outer Polymer-Plasticizer Shells The Licorice Root Extract encapsulated by proposed procedure was natural extract standardized by content of active principle Glabridin (flavonoid) and obtained from Licorice Root (*Glycyrrhiza Glabra*) root by organic solvent extraction.

At the first stage, cores containing Licorice Extract coated with a polymer-plasticizer shell were prepared by dissolving 7 g poly(methyl methacrylate)-co-(methacrylic acid) (1:0.16) in 50 ml ethyl acetate while stirring for a period of 10 min at a temperature of 40° C. The solution was cooled to room temperature, followed by addition of 1 g antioxidant (chosen from BHA, BHT or the mixture thereof), which was preliminarily dissolved in 10 ml ethyl acetate while stirring for a period of 5 min, 3 g Licorice Extract (Maruzen Pharmaceuticals Co. Ltd.) and 9 g plasticizer (chosen from tricaprylin, acetyl triethyl citrate or the mixture thereof), while stirring for a period of 5 min. The prepared organic solution was stirred for 30 min and poured into 340 ml of water containing 1 g PVA, previously saturated with 40 ml ethyl acetate, while stirring. The obtained emulsion was poured into 2 L of water containing 1 g PVA, and incubated for 10-15 min for extraction of ethyl acetate and microcapsule formation. The obtained core microcapsules were isolated by sedimentation, washed with water, and dried at 20° C. to produce a free flowing powder. The outer diameter of these core microcapsules was in the range of 20-60 µm.

At the second stage, in order to treat the core surface before coating with an outer shell, 20 g of the obtained cores were powdered with 0.16 g Aerosil 200.

At the third stage, the powdered modified inner cores containing encapsulated Licorice Extract coated with a polymer-plasticizer shell, were coated with a second polymer-plasticizer shell according to the following procedure:

The polymer-plasticizer solution was prepared by dissolving 5 g of poly(methyl methacrylate)-co-(methacrylic acid) (1:0.16) in 57 ml ethyl acetate while stirring for a period of 10 min at a temperature 40° C., and then the solution was cooled, followed by addition of 4 g plasticizer (chosen from tricaprylin, acetyl triethyl citrate or the mixture thereof) and 1 g antioxidant (chosen from BHA, BHT or mixture thereof). Afterwards, the solution was stirred for a period of 10 min. The polymer-plasticizer solution was emulsified in 170 ml of water containing 1 g PVA saturated with 20 ml ethyl acetate. Then, 20 g of the powdered modified cores were added to the obtained emulsion and dispersed for a period of 10 min. The obtained multi-component emulsion was poured into 2 L of water, while stirring, and incubated for 15 min for extraction of ethyl acetate and formation of double-layered microcapsules. The isolation of the double-layered microcapsules as a free flowing powder was performed as described in stage one. The outer diameter of the double-layered microcapsules was in the range of 60-90 µm.

Example 18

Encapsulation of Tea Tree Oil (*Melaleuca Alternifolia*) into Double-Layered Microcapsules with Inner and Outer Polymer-Plasticizer Shells At the first stage, the inner cores with the encapsulated Tea Tree Oil coated with a polymer-plasticizer shell were prepared by adding 8 g natural Tea Tree Oil (Bronson and Jacobs) and 6 g plasticizer (chosen from isopropyl myristate, triethyl citrate, tricaprylin or a mixture thereof) to a solution of 6 g poly(methyl methacrylate)-co-(methacrylic acid) (1:0.16) dissolved in 74 ml ethyl acetate. This solution was poured while stirring into 400 ml of water containing 2 g PVA, which was beforehand saturated with 44 ml ethyl acetate. The obtained emulsion was poured into 3 L of water containing 15 g PVA, and incubated for 10-15 min to extract ethyl acetate and microcapsule formation. The formed core microcapsules were isolated by sedimentation, washed and dried at a temperature not higher than 20° C. to get a free flowing powder. The outer diameter of the microcapsules was in the range of 10-50 µm.

At the second stage, in order to prepare the core surface for coating with the outer shell, 20 g of the obtained inner core microcapsules were powdered with 0.3 g Aerosil-200.

At the third stage, the powdered modified inner cores containing Tea Tree Oi coated with a polymer-plasticizer shell, were coated with a second polymer-plasticizer shell as follows: 1 g plasticizer (chosen from trilaurin, tricaprylin, tripalmitin or a mixture thereof) and 1 g poly(methyl methacrylate)-co-(methacrylic acid) (1:0.16) were dissolved in 55 ml ethyl acetate while stirring for a period of 10 min. This polymer-plasticizer solution was emulsified in 160 ml of water containing 1 g of PVA saturated beforehand with 18 ml ethyl acetate. To the obtained emulsion, 20 g of powdered modified inner cores were added and dispersed for 10 min. The obtained multi-component emulsion was poured into 2 L of containing 1 g of PVA, while stirring, and the system was incubated for 15 min to extract ethyl acetate and allow formation of the double-layered microcapsules. The isolation of the double-layered microcapsules as a free flowing powder was performed as described in stage one. The outer diameter of these microcapsules was in the range of 40-60 µm.

Example 19

Encapsulation of Rutin into Double-Layered Microcapsules with Inner and Outer Polymer-Plasticizer Shells Rutin (vitamin P) is biologically active ingredient has flavonoids structure, which isolated from plan extracts source.

At the first stage, Rutin containing cores coated with a polymer-plasticizer shell were prepared by dissolving 10 g of poly(methyl methacrylate)-co-(methacrylic acid) (1:0.16) in 47 ml ethyl acetate while stirring for a period of 10 min at a temperature of 40° C., and then the solution was cooled to room temperature, followed by addition of 2 g Eudragit RS PO (Degussa), 1 g antioxidant (chosen from BHA, BHT or a mixture thereof), 5 g plasticizer (chosen from trilaurin, acetyl triethyl citrate or a mixture thereof) and 2 g of Rutin Hydrate (RES PHARMA), which was beforehand dispersed in 20 ml ethyl acetate, while stirring. Afterwards, the prepared organic solution was stirred for a period of 30 min and poured into 400 ml of distilled water containing 2 g PVA, previously saturated with 44 ml ethyl acetate, while stirring. The obtained emulsion was poured into 3 L of distilled water and incubated for 10-15 min to extract ethyl acetate and allow formation of the core microcapsules. The obtained core microcapsules were isolated by sedimentation, washed with distilled water, and dried at a temperature not higher than 20° C. to get a free flowing powder. The outer diameter of the core microcapsules was in the range of 20-60 µm.

At the second stage, in order to prepare the core surface for coating with an outer shell, 20 g of the obtained inner core microcapsules were powdered with 0.16 g Aerosil 200.

At the third stage, the powdered modified inner cores containing encapsulated Rutin coated with a polymer-plasticizer shell were coated with a second polymer-plasticizer shell as follows: The polymer-plasticizer solution was prepared by dissolving 1 g poly(methyl methacrylate)-co-(methacrylic acid) (1:0.16) in 57 ml ethyl acetate while stirring for a period of 10 min at a temperature of 40° C., and then the solution was cooled, followed by addition of 1 g Eudragit RS PO, 1 g antioxidant (chosen from BHA, BHT or a mixture thereof) and 0.5 g plasticizer (chosen from isopropyl myristate, tricaprylin, acetyltriethyl citrate or a mixture thereof). Afterwards, the solution was stirred for a period of 10 min. The polymer-plasticizer solution was beforehand emulsified in 170 ml distilled water containing 1 g PVA saturated with 19 ml ethyl acetate. Then, 20 g of powdered modified inner cores were added to the obtained emulsion and dispersed for a period of 10 min. The obtained multi-component emulsion was poured into 2 L of distilled of water, while stirring, and incubated for 15 min to extract ethyl acetate and allow formation of double-layered microcapsules. The isolation of the double-layered microcapsules as a free flowing powder was performed as described in stage one. The outer diameter of the double-layered Rutin microcapsules was in the range of 60-100 µm.

Example 20

Encapsulation of Menthol into Composite Double-Layered Microcapsules with Inner Polymer-Plasticizer Shell and Outer Polymer-Mineral Shell At the first stage, the inner cores containing Menthol coated with a polymer-plasticizer shell were prepared by adding 4 g of Menthol (AMC Chemicals (UK) Ltd.) and 7 g plasticizer (chosen from tricaprylin, triethyl citrate, isopropyl myristate or a mixture thereof) to a solution of 9 g poly (methyl methacrylate)-co-(methacrylic acid) (1:0.16) in 60 ml ethyl acetate while stirring. This solution was poured while stirring into 167 ml of water containing 0.5 g PVA, which was beforehand saturated with 19 ml ethyl acetate. The obtained emulsion was poured into 2 L of water containing 5 g PVA, while stirring, and incubated for 10-15 min at 20° C. to extract ethyl acetate and allow formation of microcapsules. The formed microcapsules were isolated by sedimentation, washed with 10% aqueous solution of ethanol and dried at a temperature not higher than 20° C. to get a free flowing powder. The outer diameter of the microcapsules was in the range of 10-40 µm.

At the second stage, in order to prepare the core surface for coating with the outer shell, 20 g of the obtained inner core microcapsules were powdered with 0.1 g Aerosil 200.

At the third stage, the powdered modified inner cores containing Menthol coated with a polymer-plasticizer shell were coated with a polymer-mineral shell as follows: The polymer-mineral dispersion was prepared by dissolving 1 g of poly (methyl methacrylate)-co-(methacrylic acid) (1:0.16) and 1 g plasticizer (chosen from trilaurin, tricaprylin, tripalmitin or a mixture thereof) in 50 ml ethyl acetate while stirring for 20 min at a temperature of 40° C. Then, the solution was cooled to room temperature, and 1 g of titanium dioxide (chosen from the mineral forms anatase, rutile, brookite or a mixture thereof) were added. Titanium dioxide was dispersed by means of ultrasonic during 2 min. Then, 20 g of the powdered modified inner cores were added to the emulsion and dispersed for a period of 10 min. The obtained polymer-mineral dispersion was immersed in 170 ml of water containing 0.4g PVA, which was beforehand saturated with 20 ml ethyl acetate. The obtained multi-component suspo-emulsion was poured into 2 L of water containing 1 g PVA and the system was incubated for 10 min to extract ethyl acetate and allow formation of composite double-layered microcapsules. The isolation of the composite microcapsules as a free flowing powder was performed as described in stage one. The outer diameter of these microcapsules was in the range of 60-80µm.

Example 21

Encapsulation of Iron Oxides Pigment into Composite Double-Layered Microcapsules with an Inner Polymer-Plasticizer Shell and an Outer Polymer-Mineral Shell At the first stage, the inner cores containing Iron Oxide pigments coated with a polymer-plasticizer shell were prepared by dissolving 2 g Eudragit RS PO (Degussa) in 15 ml ethyl acetate while stirring for a period of 10 min. Then 2 g of plasticizer (chosen from tricaprylin, triethyl citrate, acetyl triethyl citrate, isopropyl myristate or the mixture thereof) were added while stirring for 5 min, followed by addition of 4 g of Iron Oxide pigments (chosen from Yellow Iron Oxide/hydroxide, Black Iron Oxide, Red Iron Oxide or the mixture thereof), while stirring for a period of 15 min. The obtained suspension was emulsified in 90 ml of water containing 0.5 g PVA saturated beforehand with 15 ml ethyl acetate. This suspension was poured into 900 ml of water, while stirring, and incubated for 10-15 min to extract ethyl acetate and allow microcapsules formation. The obtained core microcapsules were isolated by sedimentation, washed with water and dried at a temperature not higher than 30° C. to get a free flowing powder.

At the second stage, 6 g of the obtained inner core microcapsules were powdered with 0.01 g Aerosil 200, before coating with additional shell.

At the third stage, a polymer-mineral dispersion was prepared by dissolving 1 g Eudragit RS PO in 15 ml ethyl acetate while stirring for a period of 5-10 min. Then, 2 g of plasticizer (chosen from tricaprylin, triethyl citrate, isopropyl myristate or the mixture thereof) were added, while stirring for 5 min, followed by addition of 11 g mineral (chosen from titanium dioxide in the form of anatase, rutile, brookite or a mixture thereof, α-modification of boron nitride, magnesium silicate, or potassium, sodium, magnesium hydroalumosilicate, magnesium myristate or mixture thereof). The obtained dispersion was treated with ultrasonic for a period of 3 min. Then, 6 g of the powdered modified inner cores containing Iron Oxide pigment coated with a polymer-plasticizer shell were gradually added to the dispersion while stirring for 5 min. After a homogenous suspension was obtained, it was emulsified in 84 ml of water containing 0.5 g PVA, saturated beforehand with 11 ml ethyl acetate. The obtained suspension was poured into 840 ml of water, while stirring, and incubated for a period of 3-5 min to extract ethyl acetate and allow formation of microcapsules. The isolation of the composite double-layered microcapsules as a free flowing powder was performed as described in stage one. The outer diameter of the double-layer microcapsules was in the range of 40-60 µm. Microscopic investigations showed that the composite double-layered microcapsules appear as white spherical particles with a smooth surface (not shown). This result indicates that the outer shell masks the color of the incorporated pigments rather efficiently.

Example 22

Encapsulation of Pigment Carmine into Composite Double-Layered Microcapsules with an Inner Polymer-Plasticizer Shell and an Outer Polymer-Mineral Shell Encapsulation of the pigment Carmine into composite double-layered microcapsules was carried out according to the following procedure:

At the first stage, the inner cores containing the pigment Carmine coated with a polymer-plasticizer shell, were prepared by dissolving 1 g poly(methyl methacrylate)-co-(methacrylic acid) (1:0.16) in 20 ml ethyl acetate while stirring for a period of 20 min at a temperature of 50° C., then the solution was cooled to room temperature. Afterwards, 2 g Eudragit RS PO were dissolved in 20 ml ethyl acetate while stirring for a period of 5 min at room temperature, and the obtained solution was poured into the first solution while stirring for 7 min. Then, 0.5 g of plasticizer (chosen from tricaprylin, triethyl citrate, isopropyl myristate or a mixture thereof) was added while stirring for a period of 3 min, followed by addition of 2 g of pigment Carmine while stirring for 3 min. Then, the suspension was treated with ultrasound for 3 min. The obtained suspension was emulsified in 150 ml of water containing 0.5 g PVA, saturated beforehand with 15 ml ethyl acetate, poured into 1 L of water, while stirring, and incubated for 10-15 min to extract ethyl acetate and allow microcapsule formation. The obtained core microcapsules were separated by sedimentation, washed with water, and dried at a temperature of 40° C. to get a free flowing powder.

At the second stage, 5 g of the obtained inner core microcapsules were powdered with 0.01 g Aerosil 200, before coating with additional shell.

At the third stage, the powdered modified inner core microcapsules containing the pigment Carmine coated with inner polymer-plasticizer shell, were coated with a polymer-mineral shell as follows:

The polymer-mineral dispersion was prepared by dissolving 15 g Eudragit RS PO in 200 ml ethyl acetate while stirring for a period of 7 min. Then, 5 g of a plasticizer (chosen from tricaprylin, triethyl citrate, isopropyl myristate or a mixture thereof) were added while stirring for a period of 3 min, and 5 g of Tween-80 were added while stirring for 3 min, followed by addition of 16 g mineral (chosen from titanium dioxide in form of anatase, rutile, brookite or a mixture thereof, α-modification of boron nitride, magnesium silicate, or potassium, sodium, magnesium hydroalumosilicate, magnesium myristate or mixture thereof) while stirring for 3 min. The obtained dispersion was treated with ultrasound for 3 min. Then, 4 g of the powdered modified inner cores containing the pigment Carmine with a polymer-plasticizer shell were gradually added into 80 g of plasticizer (chosen from tricaprylin, triethyl citrate, paraffin oil or a mixture thereof) while stirring for 3 min. After homogenous suspension was obtained it was emulsified in 2 L of water containing 0.5 g PVA, saturated beforehand with 150 ml ethyl acetate. The obtained suspo-emulsion was poured into 9 L of water while stirring and incubated for 15 min at a temperature of 10° C. to extract ethyl acetate and allow microcapsule formation. The isolation of composite double-layered microcapsules as a free flowing powder was performed as described in stage one, followed by additional washing with water at a temperature of 10° C. and drying at a temperature of 20° C. The outer diameter of the obtained microcapsules was in the range of 40-60 µm. Microscopic investigation showed that these composite double-layered microcapsules appear as white-pink spherical microparticles with a smooth surface (not shown). This result indicates that the outer shell masks the color of the incorporated pigment rather efficiently.

Example 23

Encapsulation of Pigment Chrome Oxide/Hydroxide into Composite Double-Layered Microcapsules with an Inner Polymer-Plasticizer Shell and an Outer Polymer-Mineral Shell At the first stage, the inner cores containing pigment Chrome Oxide (Green)/Hydroxide (Blue) were prepared by dissolving 2.5 g Eudragit RS PO in 15 ml ethyl acetate while stirring for a period of 10 min. Then, 1.5 g of plasticizer (chosen from tricaprylin, triethyl citrate, acetyl triethyl citrate, isopropyl myristate or the mixture thereof) were added while stirring for 5 min, followed by addition of 5 g of Chrome Oxide (Green)/Hydroxide (Blue) while stirring for a period of 15 min. The obtained suspension was emulsified in 85 ml water containing 0.3 g PVA, saturated beforehand with 16 ml ethyl acetate. This suspension was poured into 850 ml of water, while stirring, and incubated for 3-5 min to extract ethyl acetate and allow microcapsule formation. The obtained core microcapsules were isolated by sedimentation, washed with fresh water and dried at a temperature not higher than 40° C. to get a free flowing powder.

At the second stage, 6 g of the inner core microcapsules containing the pigment were powdered with 0.05 g Aerosil 200, before coating with an outer shell.

At the third stage, the powdered modified inner cores containing Chrome Oxide (Green)/Hydroxide (Blue) coated with the inner polymer-plasticizer shell, were coated with a polymer-mineral shell as follows: The polymer-mineral dispersion was prepared by dissolving 2 g Eudragit RS PO in 15 ml ethyl acetate while stirring for 5-10 min. Then, 1 g plasticizer (chosen from tricaprylin, triethyl citrate, isopropyl myristate or the mixture thereof) were added while stirring for 5 min, followed by addition of 11 g of a mineral (chosen from titanium dioxide in form of anatase, rutile, brookite or a mixture thereof, $\alpha$-modification of boron nitride, magnesium silicate, or potassium, sodium, magnesium hydroalumosilicate, magnesium myristate or mixture thereof). The obtained dispersion was treated with ultrasound for a period of 3 min. Then, 6 g of the powdered modified inner cores containing pigment Chrome Oxide (Green)/Hydroxide (Blue) within were gradually added to the dispersion while stirring for 5 min. After a homogeneous suspension was obtained, it was emulsified in 85 ml of water containing 0.3 g PVA, saturated beforehand with 12 ml ethyl acetate. The obtained suspension was poured into 850 ml of water, while stirring, and incubated for a 3-5 min to extract ethyl acetate and allow microcapsule formation. The isolation of the composite double-layered microcapsules as a free flowing powder was performed as described in stage one. The outer diameter of the double-layer microcapsules was in the range of 40-60 μm. Microscopic investigations showed that the composite double-layered microcapsules appear as white spherical particles with a smooth surface. This result indicates that the outer shell masks the color of the incorporated pigments rather efficiently.

Example 24

Encapsulation of D&C Red 21 Aluminum Lake into Composite Double-Layered Microcapsules with an Inner Polymer-Plasticizer Shell and an Outer Polymer-Mineral Shell At the first stage, the inner cores containing D&C Red 21 Aluminum Lake (Fluoran) within were prepared by dissolving 1 g poly(methyl methacrylate)-co-(methacrylic acid) (1:0.16) in 30 ml ethyl acetate while stirring for a period of 20 min at a temperature of 50° C., and then the solution was cooled to room temperature. 2 g of Eudragit RS PO were dissolved in 30 ml ethyl acetate while stirring for a period of 5 min at room temperature and this solution was poured into the first solution while stirring for 7 min. Then, 3 g of a plasticizer (chosen from tricaprylin, triethyl citrate, trilaurin, isopropyl myristate or a mixture thereof) was added while stirring for 3 min, followed by addition of 4 g D&C Red 21 Aluminum Lake while stirring for additional 3 min and, the suspension was treated with ultrasound for 3 min. The obtained suspension was emulsified in 300 g of water containing 0.8 g PVA, saturated beforehand with 37 ml ethyl acetate. The obtained suspension was poured into 2 L of water, while stirring, and incubated for 10-15 min to extract ethyl acetate and allow microcapsule formation. The obtained core microcapsules were isolated by sedimentation, washed with water and dried at a temperature of 40° C. to get a free flowing powder.

At the second stage, in order to treat the core surface before coating with an outer shell, 5 g of obtained core microcapsules were powdered with 0.01 g of Aerosil 200.

At the third stage, the powdered modified inner cores containing D&C Red. 21 Aluminum Lake coated with a polymer-plasticizer shell were coated with a polymer-mineral shell as follows: A polymer-mineral dispersion was prepared by dissolving 5 g Eudragit RS PO in 120 ml ethyl acetate while stirring for a period of 7 min, then 4 g of a plasticizer (chosen from tricaprylin, triethyl citrate, isopropyl myristate or a mixture thereof) were added while stirring for 3 min, and 4 g of Tween-80 were added while stirring for additional 3 min, followed by addition of 7 g of a mineral (chosen from titanium dioxide in the form of anatase, rutile, brookite or a mixture thereof, $\alpha$-modification of boron nitride, magnesium silicate, or potassium, sodium, magnesium hydroalumosilicate, magnesium myristate or mixture thereof) and stirring for 3 min. The obtained dispersion was treated with ultrasound for 3 min. Then, 4 g of the powdered modified inner cores containing D&C Red 21 Aluminum Lake within were gradually added into 70 g of a plasticizer (chosen from tricaprylin, triethyl citrate, acetyl triethyl citrate, paraffin oil or a mixture thereof) while stirring for a period of 3 min. This mixture was added to the dispersion while stirring for 3 min. After a homogeneous suspension was obtained, it was emulsified in 800 ml of water containing 4 g PVA saturated beforehand with 100 ml ethyl acetate. The obtained suspo-emulsion was poured into 5 L of water, while stirring, and incubated for a period of 15 min at 10° C. to extract ethyl acetate and allow microcapsule formation. The procedure of isolation of the composite double-layered microcapsules as a free flowing powder was performed as described in stage one, followed by additional washing with water at a temperature of 10° C. and drying at a temperature of 20° C. The outer diameter of the double-layer microcapsules was in the range of 40-60 μm.

Example 25

Encapsulation of Colorant D&C Green 6 Liposoluble into Composite Double-Layered Microcapsules with an Inner Polymer-Plasticizer Shell and an Outer Polymer-Mineral Shell At the first stage, the inner cores containing Colorant D&C Green 6 Liposoluble within were prepared by dissolving 1 g poly(methyl methacrylate)-co-(methacrylic acid) (1:0.16) in 20 ml ethyl acetate while stirring for a period of 20 min at a temperature of 50° C., and the solution was cooled to room temperature. 3 g of Eudragit RS PO were dissolved in 20 ml ethyl acetate while stirring for a period of 5 min at room temperature and this solution was poured into the first solution while stirring for 7 min. Then, 10 g of a plasticizer (chosen from tricaprylin, triethyl citrate, trilaurin, isopropyl myristate, block copolymer of ethylene oxide and propylene oxide, magnesium silicate or a mixture thereof) was added while stirring for 3 min, followed by addition of 10 g of Colorant D&C Green 6 Liposoluble while stirring for additional 3 min, and then the suspension was treated with ultrasound for 3 min. The obtained suspension was emulsified in 250 ml water containing 1.5 g PVA, saturated beforehand with 32 ml ethyl acetate. The obtained suspension was poured into 2 L of water, while stirring, and incubated to extract ethyl acetate and allow microcapsule formation. The obtained core microcapsules were separated by sedimentation, washed with water and dried at a temperature of 20° C. to get a free flowing powder.

At the second stage, in order to treat the core surface before coating with an outer shell, 10 g of the obtained core microcapsules were powdered with 0.1 g of magnesium silicate.

At the third stage, the powdered modified inner cores containing Colorant D&C Green 6 Liposoluble coated with the inner polymer-plasticizer shell, were coated with a polymer-mineral shell as follows: The polymer-mineral dispersion was prepared by dissolving 1 g Eudragit RS PO in 30 ml ethyl acetate while stirring for a period of 7 min, then 1 g of a plasticizer (chosen from tricaprylin, triethyl citrate, isopropyl myristate or a mixture thereof) were added while stirring for 3 min, followed by addition of 7 g of a mineral (chosen from titanium dioxide in form of anatase, rutile, brookite or a mixture thereof, α-modification of boron nitride, magnesium silicate, or potassium, sodium, magnesium hydroalumosilicate. Magnesium myristate or mixture thereof) and stirring for 3 min. The obtained dispersion was treated with ultrasound for 3 min. Then, 7 g of the powdered modified inner cores containing Colorant D&C Green 6 Liposoluble within were gradually added to the dispersion while stirring for 3 min. After a homogeneous suspension was obtained, it was emulsified in 200 ml of water containing 1 g PVA, saturated beforehand with 20 ml ethyl acetate. The obtained suspo-emulsion was poured into 2 L of water, while stirring, and incubated for a period of 15 min at 10° C. to extract ethyl acetate and allow microcapsule formation. The procedure of isolation of the composite double-layer microcapsules as a free flowing powder was performed as described in stage one, followed by additional washing with water at a temperature of 10° C. and drying at a temperature of 20° C. The outer diameter of the double-layer microcapsules was in the range of 40-60 μm.

Example 26

Encapsulation of D&C Red 7 Calcium Lake into Composite Double-Layered Microcapsules with an Inner Polymer-Plasticizer Shell and an Outer Polymer-Mineral Shell At the first stage, the inner cores containing D&C Red 7 Calcium Lake were prepared by dissolving 3 g Eudragit RS PO in 15 ml ethyl acetate while stirring for a period of 10 min. Then, 1 g of plasticizer (chosen from tricaprylin, triethyl citrate, acetyl triethyl citrate, isopropyl myristate or the mixture thereof) were added while stirring for 5 min, followed by addition of 6 g of D&C Red 7 Calcium Lake while stirring for 15 min. The obtained suspension was emulsified in 84 ml water containing 0.5 g PVA, saturated beforehand with 15 ml ethyl acetate, and poured into 840 ml of water, while stirring, and incubated to extract ethyl acetate and allow microcapsule formation. The obtained core microcapsules were isolated by sedimentation, washed with water and dried at a temperature not higher than 40° C. to get a free flowing powder.

At the second stage, in order to treat the core surface before coating with an outer shell, 3 g of the obtained core microcapsules were powdered with 0.1 g of magnesium silicate.

At the third stage, the obtained modified inner core microcapsules containing D&C Red 7 Calcium Lake coated with a polymer-plasticizer shell, were coated with a polymer-mineral shell as follows: The polymer-mineral dispersion was prepared by dissolving 1 g Eudragit RS PO in 15 ml ethyl acetate while stirring for a period of 5-10 min, then 1 g of plasticizer (chosen from tricaprylin, triethyl citrate, isopropyl myristate or the mixture thereof) were added while stirring for 5 min, followed by addition of 7 g of titanium dioxide (in form of anatase, rutile, brookite or mixture thereof). The obtained dispersion was treated with ultrasound for a period of 3 min. Then, 1 g of the core microcapsules containing D&C Red 7 Calcium Lake within were gradually added to the dispersion while stirring for 5 min. After a homogeneous suspension was obtained, it was emulsified in 84 ml of water containing 0.5 g PVA, saturated beforehand with 11 ml ethyl acetate. The obtained suspension was poured into 840 ml of water, while stirring, and incubated for a period of 3-5 min to extract ethyl acetate and allow microcapsule formation. The isolation of the composite double-layered microcapsules as a free flowing powder was performed as described in stage one. The outer diameter of the microcapsules was in the range of 50-70 μm.

Example 27

Encapsulation of Pigment Aluminium Blue #1 (Indigo Carmine Lake) into Composite Triple-Layered Microcapsules with a First Inner Polymer-Plasticizer Shell, a Second Inner Polymer-Mineral Shell and an Outer Polymer-Mineral Shell At the first stage, the inner core microcapsules containing pigment Aluminium Blue #1 (Indigo Carmine Lake) within, were prepared by dissolving 2 g of poly(methyl methacrylate)-co-(methacrylic acid) (1:0.16) in 40 ml ethyl acetate while stirring for a period of 20 min at a temperature of 50° C., then the solution was cooled to room temperature. Afterwards, 4 g Eudragit RS PO were dissolved in 40 ml ethyl acetate while stirring for a period of 5 min at room temperature and the obtained solution was poured into the first solution while stirring for 7 min. Then, 1 g of plasticizer (chosen from tricaprylin, triethyl citrate, isopropyl myristate or a mixture thereof) was added while stirring for a period of 3 min, followed by addition of 6 g of pigment Aluminium Blue #1 (Indigo Carmine Lake) while stirring for 3 min. Then, the suspension was treated with ultrasound for 3 min. The obtained suspension was emulsified in 300 ml of water containing 1 g PVA, saturated beforehand with 30 ml ethyl acetate, poured into 2 L of water, while stirring, and incubated to extract ethyl acetate and allow microcapsule formation. The obtained core microcapsules were separated by sedimentation, washed with water, and dried at a temperature of 20° C. to get a free flowing powder.

At the second stage, 10 g of the obtained core microcapsules were powdered with 0.05 g Aerosil-200 before coating with an outer shell.

At the third stage, the powdered modified core microcapsules containing pigment Aluminium Blue #1 (Indigo Carmine Lake), were coated with a polymer-mineral shell as follows: The polymer-mineral dispersion was prepared by dissolving 15 g Eudragit RS PO in 200 ml ethyl acetate while stirring for a period of 7 min, then 5 g of plasticizer (chosen from tricaprylin, triethyl citrate, isopropyl myristate or a mixture thereof) were added while stirring for a period of 3 min, and 5 g of Tween-80 were added while stirring for 3 min, followed by addition of 16 g of a mineral (chosen from titanium dioxide in form of anatase, rutile, brookite or a mixture thereof, $\alpha$-modification of boron nitride, magnesium silicate, or potassium, sodium, magnesium hydroalumosilicate, magnesium myristate or mixture thereof) while stirring for 3 min. The obtained dispersion was treated with ultrasound for 3 min. Then, 6 g of the powdered modified inner cores containing pigment Aluminium Blue #1 (Indigo Carmine Lake) within were added gradually into 80 g of a plasticizer (chosen from tricaprylin, triethyl citrate, paraffin oil or a mixture thereof) while stirring for 3 min. After a homogeneous suspension was obtained, it was emulsified in 2 L of water containing 10 g PVA, saturated beforehand with 150 ml ethyl acetate. The obtained suspo-emulsion was poured into 9 L of water, while stirring, and incubated for 15 min at a temperature of 10° C. to extract ethyl acetate and allow microcapsule formation. The isolation of composite double-layered microcapsules as a free flowing powder was performed as described in stage one, followed by additional washing with water at a temperature of 10° C. and drying at a temperature of 20° C.

At the fourth stage, 20 g of composite double-layered microcapsules from the third stage were powdered with 0.2 g magnesium silicate before coating with an additional outer shell.

At the fifth stage, the powdered modified microcapsules from the fourth stage, were coated with an additional polymer-mineral shell as follows: The polymer-mineral dispersion was prepared by dissolving 2 g Eudragit RS PO in 100 ml ethyl acetate while stirring for a period of 7 min. Then, 4 g of a plasticizer (chosen from tricaprylin, triethyl citrate, isopropyl myristate or a mixture thereof) were added while stirring for a period of 3 min, followed by addition of 5 g of a mineral (chosen from titanium dioxide in form of anatase, rutile, brookite or a mixture thereof, $\alpha$-modification of boron nitride, magnesium silicate, or potassium, sodium, magnesium hydroalumosilicate, magnesium myristate or mixture thereof) while stirring for 3 min. The obtained dispersion was treated with ultrasound for 3 min. Then, 20 g of the powdered modified microcapsules from the fourth stage were added gradually to the dispersion while stirring for a period of 3 min. After a homogeneous suspension was obtained, it was emulsified in 600 ml of water containing 3 g PVA, saturated beforehand with 60 ml ethyl acetate. The obtained suspo-emulsion was poured into 5 L of water, while stirring, and incubated for 15 min at a temperature of 10° C. to extract ethyl acetate and allow microcapsule formation. The isolation of composite triple-layered microcapsules as a free flowing powder was performed as described in stage one, followed by additional washing with water at a temperature of 10° C. and drying at a temperature of 20° C. The outer diameter of the obtained microcapsules was in the range of 70-90 μm.

The invention claimed is:

1. A method for the production of double-layer and triple-layer microcapsules for topical application,
wherein the microcapsules consist of an inner core microcapsule which contains an active ingredient located within a wall-forming polymer shell and one or two outer shells of the same or different wall-forming polymer coating the inner core microcapsule,
said method comprising the steps of:
(a) dissolving or dispersing the active ingredient, optionally together with an antioxidant, a plasticizer or both, in ethyl acetate, together with a wall-forming polymer selected from the group consisting of a polyacrylate, a polymethacrylate, low molecular weight poly(methyl methacrylate)-co-(methacrylic acid) (1:0.16), poly (ethyl acrylate)-co-(methyl methacrylate)-co-(trimethylammonium-ethyl methacrylate chloride) (1:2:0.1), poly(butyl methacrylate)-co-(2-dimethylaminoethyl methacrylate)-co-(methyl methacrylate) (1:2:1), poly (styrene)-co-(maleic anhydride), copolymer of octylacrylamide, cellulose ethers, cellulose esters and poly (ethylene glycol)-block-poly(propylene glycol)-block-poly(ethylene glycol), to form an organic solution or dispersion;
(b) preparing an aqueous continuous phase saturated with said ethyl acetate and comprising an emulsifier;
(c) while agitating, pouring an amount sufficient of the organic solution or dispersion obtained in (a) into the aqueous continuous phase obtained in (b), to form an emulsion;
(d) adding an excess amount of water to the emulsion obtained in (c) sufficient to initiate extraction of the ethyl acetate from the emulsion, and optionally incubating for further extraction of the ethyl acetate and formation of solid microcapsules (hereinafter "the inner core microcapsules");
(e) either (i) isolating the inner core microcapsules, washing with water and drying, or (ii) immersing the core microcapsules into an aqueous solution of alcohol, separating the core microcapsules and drying;
(f) treating the surface of the dried inner core microcapsules obtained in (e) with a material that modifies the morphology of the surface, increases its specific surface area and facilitates the adhesion of an additional polymeric shell, thus obtaining microcapsules powdered with said material (hereinafter "powdered modified inner cores");
(g) dissolving or dispersing a wall-forming polymer with a plasticizer or a mineral in ethyl acetate, to form a polymer-plasticizer solution or polymer-mineral dispersion;
(h) preparing an aqueous continuous phase saturated with said ethyl acetate and comprising an emulsifier;
(i) while agitating, pouring the polymer-plasticizer solution or polymer-mineral dispersion obtained in step (g)

into the aqueous continuous phase obtained in step (h), to form a polymer-plasticizer emulsion or a polymer-mineral suspo-emulsion;

(j) while agitating, immersing the powdered modified inner cores obtained in step (f) into the polymer-plasticizer emulsion or polymer-mineral suspo-emulsion obtained in step (i), forming a multi-component emulsion or a new suspo-emulsion, in which a formation of "embryo" shells around said core microcapsules is initiated;

(k) while stirring, either (i) adding an excess amount of water to the multi-component emulsion or the new suspo-emulsion obtained in step (j), or (ii) pouring the multi-component emulsion or the new suspo-emulsion obtained in step (j) into water, and incubating the system for extraction of the ethyl acetate from said multi-component emulsion or suspo-emulsion, and conversion of the "embryo" shell into a solid polymer wall and formation of double-layer microcapsules;

(l) separating the obtained double-layer microcapsules from water and drying the wet capsules, thereby isolating double-layer microcapsules as a free flowing powder; and (m) optionally, to form three layers, repeating steps (f) to (l) to form one additional layer around the double-layer microcapsules, thereby obtaining triple-layer microcapsules.

2. The method according to claim 1, wherein said active ingredient is at least one agent having biological activity, an odor agent or a color agent.

3. The method according to claim 2, wherein said agent having biological activity is selected from the group consisting of vitamins, natural extracts, individual compounds isolated from natural sources, essential oils, and pharmaceutical agents for topical application.

4. The method according to claim 3, wherein said vitamin is vitamin A, B, C, D, E, F, K, P, or mixtures thereof.

5. The method according to claim 4, wherein said vitamin A is Retinol or Retinol Palmitate, said vitamin E is α-tocopherol, said vitamin F is a mixture of linoleic and linolenic acids, and said vitamin P is Rutin.

6. The method according to claim 3, wherein said natural extract is Licorice extract, Grape Seed extract, Evening Primrose Oil, Borage Oil, or Hippophae Oil.

7. The method according to claim 3, wherein said individual compound isolated from a natural source is a coumarin, a chalcone or a flavonoid selected from the group consisting of flavans, flavanols, flavonols, flavones, flavanones, isoflavones, anthocyanidins, and proanthocyanidins.

8. The method according to claim 3, wherein said flavonoid is Rutin.

9. The method according to claim 3, wherein said essential oil is Basil Essential Oil, Eucalyptus Essential Oil, Geranium Essential Oil, Grapefruit Essential Oil, Lemon Essential Oil, Peppermint Essential Oil, Tea Tree Oil, or mixtures thereof.

10. The method according to claim 3, wherein said pharmaceutical agent for topical application is an antibiotic.

11. The method according to claim 10, wherein said antibiotic is a macrolide antibiotic selected from the group consisting of Erythromycin, Azithromycin or Clarithromycin.

12. The method according to claim 2, wherein said odor agent is selected from the group consisting of fragrances, perfumes, essential oils, and volatile natural and synthetic compounds.

13. The method according to claim 12, wherein said volatile compound is Menthol.

14. The method according to claim 2, wherein said color agent is selected from the group consisting of organic and inorganic pigments, colorants and color agents from natural source.

15. The method according to claim 14, wherein said color agent is at least one agent selected from the group consisting of Carmine, iron oxides, titanium dioxide, chrome oxide/hydroxide, D&C Red 21 Aluminum Lake, D&C Red 7 Calcium Lake, D&C Green 6, Liposoluble, and Aluminium Blue #1, and mixtures thereof.

16. The method according to claim 1, wherein the wall-forming polymer shell is a polymer-plasticizer or polymer-mineral shell.

17. The method according to claim 16, wherein the inner and outer polymer shells are both polymer-plasticizer shells and the polymer of the inner core microcapsule and of the outer shells are identical.

18. The method according to claim 16, wherein the inner and outer polymer shells are both polymer-plasticizer shells and the polymer of the inner core microcapsule and of the outer shells are different.

19. The method according to claim 16, wherein the inner and outer polymer shells are both polymer-mineral shells and the polymer of the inner core microcapsule and of the outer shells are identical.

20. The method according to claim 16, wherein the inner and outer polymer shells are both polymer-mineral shells and the polymer of the inner core microcapsule and of the outer shells are identical.

21. The method according to claim 16, wherein the inner polymer shell is a polymer-plasticizer shell and the outer polymer shell is a polymer-mineral shell or the inner polymer shell is a polymer-mineral shell and the outer polymer shell is a polymer-plasticizer shell and the polymers of both shells are identical.

22. The method according to claim 16, wherein the inner polymer shell is a polymer-plasticizer shell and the outer polymer shell is a polymer-mineral shell or the inner polymer shell is a polymer-mineral shell and the outer polymer shell is a polymer-plasticizer shell and the polymers of the inner and of the outer shells are different.

23. The method according to claim 1, wherein said wall-forming polymer is ethyl cellulose, low molecular weight poly(methyl methacrylate)-co-(methacrylic acid) (1:0.16), poly(ethyl acrylate)-co-(methyl methacrylate)-co-(trimethylammonium-ethyl methacrylate chloride) (1:2:0.1), or a mixture thereof.

24. The method according to claim 1, wherein said plasticizer that forms the polymer-plasticizer solution in step (g) is selected from the group consisting of tricaprylin, trilaurin, tripalmitin, triacetin, triethyl citrate, acetyltriethyl citrate, isopropyl myristate, paraffin oil, and mixtures thereof.

25. The method according to claim 1, wherein said mineral that forms the polymer-mineral dispersion in step (g) is selected from the group consisting of titanium dioxide, boron nitride, magnesium silicate, potassium, sodium, magnesium hydroalumosilicate, and mixtures thereof.

26. The method according to claim 1, wherein said material in step (f) that changes the morphology of the core surface and increases the specific surface area is dioxosilicon or magnesium silicate.

27. The method according to claim 1, wherein the core microcapsule contains more than one active ingredient or said active ingredient is in mixture with an anti-oxidant.

28. Triple-layer microcapsules for topical application, consisting of an inner core microcapsule which contains an active ingredient located within a wall-forming polymer, and two more outer shells of the same or different wall-forming polymer coating the inner core microcapsule, wherein said triple-layer microcapsules are obtained according to the method of claim 1.

29. Triple-layer microcapsules according to claim 28, wherein the outer diameter of the inner core microcapsule is in the range of 1-100 μm and the outer diameter of the triple-layer microcapsule is in the range of 10-200 μm.

30. Triple-layer microcapsules according to claim 29, wherein said outer diameter of the triple-layer microcapsule is in the range of 30-50 μm.

31. Double-layer microcapsules for topical application, consisting of an inner core microcapsule which contains an active ingredient located within a wall-forming polymer, and one outer shell of the same or different wall-forming polymer coating the inner core microcapsule, wherein said double-layer microcapsules are obtained according to the method of claim 1.

32. Double-layer microcapsules according to claim 31, wherein said active ingredient is at least one agent having biological activity, an odor agent or a color agent.

33. Double-layer microcapsules according to claim 32, wherein said agent having biological activity is selected from the group consisting of vitamins, natural extracts, individual compounds isolated from natural sources, essential oils, and pharmaceutical agents for topical application.

34. Double-layer microcapsules according to claim 33, wherein said vitamin is vitamin A, B, C, D, E, F, K, P, or mixtures thereof.

35. Double-layer microcapsules according to claim 34, wherein said vitamin A is Retinol or Retinol Palmitate, said vitamin E is α-tocopherol, said vitamin F is a mixture of linoleic and linolenic acids, and said vitamin P is Rutin.

36. Double-layer microcapsules according to claim 33, wherein said natural extract is Licorice extract, Grape Seed extract, Evening Primrose Oil, Borage Oil, or Hippophae Oil.

37. Double-layer microcapsules according to claim 33, wherein said individual compound isolated from a natural source is a coumarin, a chalcone or a flavonoid selected from the group consisting of flavans, flavanols, flavonols, flavones, flavanones, isoflavones, anthocyanidins, and proanthocyanidins.

38. Double-layer microcapsules according to claim 37, wherein said flavonoid is Rutin.

39. Double-layer microcapsules according to claim 33, wherein said essential oil is Basil Essential Oil, Eucalyptus Essential Oil, Geranium Essential Oil, Grapefruit Essential Oil, Lemon Essential Oil, Peppermint Essential Oil, Tea Tree Oil, or mixtures thereof.

40. Double-layer microcapsules according to claim 33, wherein said pharmaceutical agent for topical application is an antibiotic.

41. Double-layer microcapsules according to claim 40, wherein said antibiotic is a macrolide antibiotic selected from the group consisting of Erythromycin, Azithromycin or Clarithromycin.

42. Double-layer microcapsules according to claim 33, wherein said odor agent is selected from the group consisting of fragrances, perfumes, essential oils, and volatile natural and synthetic compounds.

43. Double-layer microcapsules according to claim 42, wherein said volatile compound is Menthol.

44. Double-layer microcapsules according to claim 32, wherein said color agent is selected from the group consisting of organic and inorganic pigments, colorants and color agents from natural source.

45. Double-layer microcapsules according to claim 44, wherein said color agent is at least one agent selected from the group consisting of Carmine, iron oxides, titanium dioxide, chrome oxide/hydroxide, D&C Red 21 Aluminum Lake, D&C Red 7 Calcium Lake, D&C Green 6 Liposoluble, and Aluminium Blue #1, and mixtures thereof.

46. Double-layer microcapsules according to claim 31, wherein the wall-forming polymer shell is a polymer-plasticizer or polymer-mineral shell.

47. Double-layer microcapsules according to claim 46, wherein the inner and outer polymer shells are both polymer-plasticizer shells and the polymer of the inner core microcapsule and of the outer shells are identical.

48. Double-layer microcapsules according to claim 46, wherein the inner and outer polymer shells are both polymer-plasticizer shells and the polymer of the inner core microcapsule and of the outer shells are different.

49. Double-layer microcapsules according to claim 46, wherein the inner and outer polymer shells are both polymer-mineral shells and the polymer of the inner core microcapsule and of the outer shells are identical.

50. Double-layer microcapsules according to claim 46, wherein the inner and outer polymer shells are both polymer-mineral shells and the polymer of the inner core microcapsule and of the outer shells are different.

51. Double-layer microcapsules according to claim 46, wherein the inner polymer shell is a polymer-plasticizer shell and the outer polymer shell is a polymer-mineral shell or the inner polymer shell is a polymer-mineral shell and the outer polymer shell is a polymer-plasticizer shell and the polymers of both shells are identical.

52. Double-layer microcapsules according to claim 46, wherein the inner polymer shell is a polymer-plasticizer shell and the outer polymer shell is a polymer-mineral shell or the inner polymer shell is a polymer-mineral shell and the outer polymer shell is a polymer-plasticizer shell and the polymers of the inner and of the outer shells are different.

53. Double-layer microcapsules according to claim 31, wherein said wall-forming polymer is ethyl cellulose, low molecular weight poly(methyl methacrylate)-co-(methacrylic acid) (1:0.16), poly(ethyl acrylate)-co-(methyl methacrylate)-co-(trimethylammonium-ethyl methacrylate chloride) (1:2:0.1), or a mixture thereof.

54. Double-layer microcapsules according to claim 46, wherein said plasticizer that forms the polymer-plasticizer shell is selected from the group consisting of tricaprylin, trilaurin, tripalmitin, triacetin, triethyl citrate, acetyltriethyl citrate, isopropyl myristate, paraffin oil, and a mixture thereof.

55. Double-layer microcapsules according to claim 46, wherein said mineral that forms the polymer-mineral shell is selected from the group consisting of titanium dioxide, boron nitride, magnesium silicate, potassium, sodium, magnesium hydroalumosilicate, mica (and) magnesium myristate, titanium dioxide (and) magnesium myristate, and mixtures thereof.

56. Double-layer microcapsules according to claim 31, wherein the core microcapsule contains more than one active ingredient or said active ingredient is in mixture with an anti-oxidant.

57. Double-layer microcapsules according to claim 47, wherein the active ingredient is Retinol, Retinol Palmitate, Licorice Extract, or Tea Tree Oil and the wall-forming polymer of the inner and outer polymer-plasticizer shells is low molecular weight poly(methyl methacrylate)-co-(methacrylic acid) (1:0.16), or the active ingredient is Rutin and the wall-forming polymer of the inner and outer polymer-plasticizer shells is a mixture of low molecular weight poly(methyl methacrylate)-co-(methacrylic acid) (1:0.16) and poly(ethyl acrylate)-co-(methyl methacrylate)-co-(trimethylammonium-ethyl methacrylate chloride) (1:2:0.1).

58. Double-layer microcapsules according to claim 51, wherein the active ingredient is Grape Seed Extract or Iron oxide pigments, and the wall-forming polymer of the inner polymer-mineral shell and of the outer polymer-plasticizer shell is poly(ethyl acrylate)-co-(methyl methacrylate)-co-(trimethyl-ammonium-ethyl methacrylate chloride) (1:2:0.1).

59. Double-layer microcapsules according to claim 51, wherein the active ingredient is Menthol and the wall-forming polymer of the inner polymer-plasticizer shell and of the outer polymer-mineral shell is low molecular weight poly (methyl methacrylate)-co-(methacrylic acid) (1:0.16).

60. Double-layer microcapsules according to claim 51, wherein the active ingredient is Chrome oxide/hydroxide pigment or D&C Red Calcium Lake and the wall-forming polymer of the inner polymer-plasticizer shell and of the outer polymer-mineral shell is poly(ethyl acrylate)-co-(methyl methacrylate)-co-(trimethyl-ammonium-ethyl methacrylate chloride) (1:2:0.1).

61. Double-layer microcapsules according to claim 52, wherein the active ingredient is Retinol, Carmine pigment, D&C Red 21 Aluminum Lake or D&C Green 6 Liposoluble, and the wall-forming polymer of the inner polymer-plasticizer shell is low molecular weight poly(methyl methacrylate)-co-(methacrylic acid) (1:0.16) and of the outer polymer-mineral shell is poly(ethyl acrylate)-co-(methyl methacrylate)-co-(trimethyl-ammonium-ethyl methacrylate chloride) (1:2:0.1).

62. Triple-layer microcapsules according to claim 28, wherein the active ingredient is Aluminum Blue #1, the wall-forming polymer of the inner polymer-plasticizer shell is a mixture of low molecular weight poly(methyl methacrylate)-co-(methacrylic acid) (1:0.16) and poly(ethyl acrylate)-co-(methyl methacrylate)-co-(trimethyl-ammonium-ethyl methacrylate chloride) (1:2:0.1), and of the two outer polymer-mineral shells is poly(ethyl acrylate)-co-(methyl methacrylate)-co-(trimethyl-ammonium-ethyl methacrylate chloride) (1:2:0.1).

63. Composition for topical application comprising triple-layer microcapsules according to claim 28.

64. Composition for topical application comprising double-layer microcapsules according to claim 31.

65. Composition comprising double-layer microcapsules according to claim 64 for skin care, skin supplement, hair care, sun care, and baby care, oral hygiene, and oral care.

66. Composition comprising double-layer microcapsules according to claim 64 for oral hygiene and oral care.

67. Composition comprising double-layer microcapsules according to claim 64 for topical application, wherein the active ingredient is a pharmaceutical.

68. Double-layer microcapsules according to claim 31, wherein the outer diameter of the inner core microcapsule is in the range of 1-100 μm and the outer diameter of the double-layer microcapsule is in the range of 10-200 μm.

69. Double-layer microcapsules according to claim 68, wherein said outer diameter of the double-layer microcapsule is in the range of 30-50 μm.

* * * * *